(12) United States Patent
Annoura et al.

(10) Patent No.: US 7,642,262 B2
(45) Date of Patent: *Jan. 5, 2010

(54) ARYLIPIPERDINOPROPANOL AND ARYLIPIPERAZINOPROPANOL DERIVATIVES AND PHARMACEUTICALS CONTAINING THE SAME

(75) Inventors: Hirokazu Annoura, Nagaokakyo (JP); Kyoko Nakanishi, Ibaraki (JP); Shigeki Tamura, Nara (JP)

(73) Assignee: Asubio Pharma Co., Ltd., Minato-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/002,793

(22) Filed: Dec. 3, 2004

(65) Prior Publication Data

US 2005/0101610 A1    May 12, 2005

Related U.S. Application Data

(62) Division of application No. 10/331,508, filed on Dec. 31, 2002, now Pat. No. 6,838,470, which is a division of application No. 10/118,045, filed on Apr. 9, 2002, now Pat. No. 6,525,199, which is a division of application No. 09/331,712, filed as application No. PCT/JP98/04943 on Oct. 30, 1998, now Pat. No. 6,407,099.

(30) Foreign Application Priority Data

Oct. 31, 1997  (JP) .................................. 9-301154

(51) Int. Cl.
*A61K 31/495* (2006.01)
*C07D 295/135* (2006.01)

(52) U.S. Cl. .................. 514/255.03; 544/394; 544/395

(58) Field of Classification Search ............. 514/255.03
See application file for complete search history.

(56) References Cited

U.S. PATENT DOCUMENTS

| | | | |
|---|---|---|---|
| 3,701,777 A | 10/1972 | Edenhofer et al. | |
| 4,859,675 A | 8/1989 | Foguet et al. | |
| 4,882,330 A | 11/1989 | Walsh et al. | |
| 5,504,087 A | 4/1996 | Ogata et al. | |
| 5,723,475 A | 3/1998 | Annoura et al. | |
| 6,048,876 A | 4/2000 | Annoura et al. | |
| 6,124,323 A | 9/2000 | Bigge et al. | |
| 6,313,127 B1 | 11/2001 | Waterson et al. | |
| 6,407,099 B1 * | 6/2002 | Annoura et al. | 514/255.03 |
| 6,455,549 B1 | 9/2002 | Annoura et al. | |
| 6,469,010 B1 | 10/2002 | Annoura et al. | |
| 6,525,199 B1 * | 2/2003 | Annoura et al. | 544/395 |
| 6,706,734 B2 | 3/2004 | Annoura et al. | |
| 6,838,470 B2 * | 1/2005 | Annoura et al. | 514/327 |

FOREIGN PATENT DOCUMENTS

| | | |
|---|---|---|
| EP | 0 031 925 | 7/1981 |
| EP | 0 576 766 | 6/1992 |
| EP | 0 755 923 A1 | 1/1997 |
| EP | 0 757 986 A1 | 2/1997 |
| EP | 0 748 800 B1 | 5/2001 |
| FR | 2112509 A | 6/1972 |
| HU | 202 494 | 6/1990 |
| JP | 53-21227 | 2/1978 |
| WO | WO96/26924 | 6/1996 |
| WO | 97/14685 A1 | 4/1997 |
| WO | 98/03172 A1 | 1/1998 |

OTHER PUBLICATIONS

Guo et al. Medline Abstract for Nature Medicine, vol. 5, p. 101-106 (1999).*
Mezetti et al. Medline Abstract for Cardiovascular Research, vol. 47, p. 475-488 (2000).*
Santi et al. Journal of Neuroscience, vol. 22, p. 396-403 (2002).*
Kupferberg Epilepsia, vol. 42 (s4), pp. 7-12 (2001).*
Grabenstatter et al. Epilepsia, vol. 46 (1), pp. 8-14 (2005).*

(Continued)

*Primary Examiner*—Emily Bernhardt
(74) *Attorney, Agent, or Firm*—Drinker Biddle & Reath LLP

(57) ABSTRACT

A compound having the formula (I) or its salt, hydrate, hydrate salt or solvate:

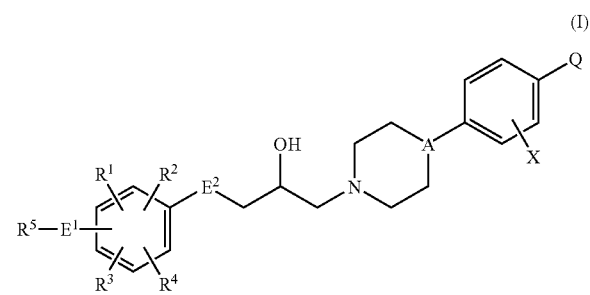

(I)

wherein $R^1$ to $R^4$ independently represent H, halogen, OH, alkoxy, optionally substituted alkyl, aryl, or aralkyl group, $R^5$ represents H, optionally substituted alkyl, aryl, or aralkyl group, $E^1$ represents O, S, or —$NR^6$, where $R^6$ represents H, an optionally substituted alkyl, aryl, or aralkyl group, $E^2$ represents O, S, or —$NR^7$, where $R^7$ represents H, an optionally substituted alkyl, aryl, or aralkyl group, A represents CH, C(OH), or N, X represents H, halogen, alkoxy, or an optionally substituted alkyl group, and Q represents an optionally substituted phenyl group, phenoxy, phenylmethyl, or cycloalkyloxy group, where when $E^1$ represents O or S, $E^2$ does not represent O or S, which has an action of suppressing the cytotoxic $Ca^{2+}$ overload and lipid peroxidation and effective for pharmaceutical preparation for the alleviation and treatment of symptoms due to ischemic diseases, etc.

7 Claims, No Drawings

OTHER PUBLICATIONS

Mattson Nature, vol. 415, p. 377-379 (2002).*

Jenner, Parkinsonism and Related Disorders, vol. 9, p. 131-137 (2003).*

Blanchet et al. Parkinsonism and Related Disorders, vol. 10, p. 297-304 (2004).*

Chemical Abstracts No. XP-002096288, Abstract of JP 760094177.

Celkova et al., Chemical Abstracts No. XP-002096287, Abstract of 127:185393; "Relationship between the structure of some 1,4-piperazine derivatives of aryloxyaminopropanols and their Ca-antagonistic activity," Pharmazie, 52(6), 1997, p. 487-488, Wiley-Interscience, New York, NY, USA.

Celkova et al., Chemical Abstracts No. XP-002096286, Abstract of 126:42254; "Piperazine analogs of aryloxyaminopropanols and studies of their effects of the model of the isolated guinea pig ileum," 1996, Ceska Slov. Farm., 45(5) pp. 255-259, U.S. National Library of Medicine, National Institutes of Health, Bethesda, MD, USA.

Grundke et al., Chemical Abstracts No. XP-002096285, Abstract of 117:40051.

"Characterization of calcium-antagonistic effects of three metabolites of the new antihypertensive agent naftopidil, (naphthyl)hydroxynaftopidil, (phenl)hydroxyl-naftopidil, and O-desmethyl-naftopidil," J. Cardiovasc. Pharmacol., 78(6), 1991, pp. 918-925, Lippincott, Williams & Wilkins, Baltimore, MD, USA.

Himmel et al., Chemical Abstracts No. XP-002096284, Abstract of 114:156847, "Naftopidil, a new .alpha.-adrenoceptor blocking agent with calcium antagonistic properties: characterization of calcium antagonistic effect," J. Cardiovasc. Pharmacol., 17(2), 1991, pp. 213-221, Lippincott, Williams & Wilkins, Baltimore, MD, USA.

Kamikawa et al., "Palladium-Catalyzed Amination of Aryl Bromides Utilizing Arene-Chromium Complexes as Ligands," 1998, pp. 8407-8410, Vol. No. 63, J. Org. Chem., The American Chemical Society, Washington, DC, USA.

Gorman et al, "The effects of cyclic terminal groups in di- and tri-arylmethane dyes. Part 3.[1] Consequences of unsymmetrical substitution in Malachite Green," 2000, pp. 1889-1895, vol. 2, J. Chem. Soc., Perkin Trans., The Royal Society of Chemistry, London, England.

Shoulson, "Experimental Therapeutics of Neurodegenerative Disorders: Unmet Needs," Science, Nov. 6, 1998, vol. 282, pp. 1072-1074 (Amer. Assn. for the Advancement of Science, Washington, DC).

Bossy-Wetzel et al., "Molecular pathways to neurodegeneration," Neurodegeneration, Jul. 2004, pp. S2-S9 (Nature Publishing Group, London, England).

Mattson et al., "Ageing and neuronal vulnerability," Nature, Apr. 2006, Vol. 7, pp. 278-294 (Nature Publishing Group, London, England).

Mattson, "Pathways towards and away from Alzheimer's disease," Nature, Aug. 5, 2004, vol. 430, pp. 631-639 (Nature Publishing Group, London, England).

Martinez et al., "Parkinson's Disease-associated α-Synuclein is a Calmodulin Substrate," The Journal of Biological Chemistry, May 9, 2003, vol. 278, No. 19, pp. 17379-17387 (American Society for Biochemistry and Molecular Biology, Baltimore, MD).

Tang et al., "Disturbed $Ca^{2+}$ signaling and apoptosis of medium spiny neurons in Huntington's disease," Proceedings of the National Academy of Sciences, Feb. 15, 2005, vol. 102, No. 7, pp. 2602-2607 (National Academy of Sciences, Washington, DC).

Von Lewinski et al., "$Ca^{2+}$, Mitochondria and selective motoneuron vulnerability: implications for ALS," Trends in Neurosciences, vol. 28, No. 9, Sep. 2005, pp. 494-500 (Elsevier Applied Science Publishing, Barking, England).

Andersen, "Oxidative stress in neurodegeneration: cause or consequence?" Neurodegeneration, Jul. 2004, pp. S18-S25 (Nature Publishing Group, London, England).

Taylor et al., "$Na^+$ channels as targets for neuroprotective drugs," Trends in Pharmacological Sciences, Sep. 1995, vol. 16, pp. 309-315 (Elsevier Science, Amsterdam, Holland).

Moosmann et al., "Antioxidants as treatment for neurodegenerative disorders," Expert Opin. Investig. Drugs (2002) 11(10), pp. 1407-1435 (Ashley Publications Ltd., London, England).

Eigyo et al., "Pharmacological Studies on a New Dihydrothienopyridine Calcium Antagonist, S-312-d $5^{th}$ Communication: Anticonvulsant Effects in Mice," Jpn. J. Pharmacol. 65, (1994), pp. 174-177 (The Japanese Pharmacological Society, Kyoto, Japan).

Ohmori et al., "6-(1$H$-Imidazol-1-yl)-7-nitro-2,3(1$H$,4$H$)-quinoxalinedione Hydrochloride (YM90K) and Related Compounds: Structure-Activity Relationships for the AMPA-Type Non-NMDA Receptor," J. Med. Chemistry, 1994, 37, pp. 467-475 (American Chemical Society, Washington, DC).

Lingamaneni et al., "Effects of anticonvulsants on veratridine- and KCl-evoked glutamate release from rat cortical synaptosomes," Neuroscience Letters 276 (1999), pp. 127-130, Elsevier, Limerick, Ireland.

Deffois et al., "Inhibition of synaptosomal veratridine-induced sodium influx by antidepressants and neuroleptics used in chronic pain," Neuroscience Letters 220 (1996) pp. 117-120, Elsevier, Limerick, Ireland.

Traynor et al., "Neuroprotective agents for clinical trials in ALS—A systematic assessment," Neurology, Jul. (1 of 2) 2006, pp. 20-27, American Academy of Neurology, Bethesda, MD.

Ravina et al., "Neuroprotective agents for clinical trials in Parkinson's disease—A systematic assessment," Neurology, Apr. (2 of 2) 2003, pp. 1234-1240, American Academy of Neurology, Bethesda, MD.

Budavari et al., "The Merk Index, An encyclopedia of chemicals, drugs, and biologicals," Twelfth Edition, 1996, p. 1395, Merck Research Laboratories, Whitehouse Station, NJ.

Meyer et al., "Calcium, Neuronal hyperexcitability and ischemic injury," Brain Research Reviews, vol. 14, 1989, pp. 227-243.

Boddeke et al., "New anti-ischaemic drugs: cytoprotective action with no protective haemodynamic effects," TiPS, Oct. 1989, vol. 10, pp. 397-400.

McCall et al., "Chapter 4. Traumatic and Ischemia/Reperfusion Indury to the CNS," Annual Reports in Medicinal Chemistry, 1992, vol. 27, pp. 31-40.

Andersson et al., "Advances in the Development of Pharmaceutical Antioxidants," Advances in Drug Research, vol. 28, pp. 1-180, (1996).

* cited by examiner

ARYLIPIPERDINOPROPANOL AND ARYLIPIPERAZINOPROPANOL DERIVATIVES AND PHARMACEUTICALS CONTAINING THE SAME

TECHNICAL FIELD

The present invention relates to novel arylpiperidinopropanol and arylpiperazinopropanol derivatives, their pharmaceutically acceptable salts, hydrates, hydrate salts and solvates effective for the alleviation and treatment of symptoms due to ischemic diseases, for example, cerebral infarction, cerebral edema, intracerebral hemorrhage, transient ischemic attack, subarachnoid hemorrhage, head trauma, after effects.of brain surgery, after effects of cerebral arteriosclerosis, and other cerebrovascular disorders, or variant angina, unstable angina, myocardial infarction, cardiovascular system disorders accompanying surgery for revascularization by PTCA (percutaneous transluminal coronary angioplasty)/PTCR (percutaneous transluminal coronary revascularization)/CABG (coronary artery bypass grafting) etc., malignant arrhythmia and myocardial ischemia-reperfusion injury, and further disorders of transplanted organs at the time of organ transplants and temporary blockage of the blood flow in organs at the time of surgery, symptoms due to neurodegenerative diseases, for example, Alzheimer's, Parkinson's and Huntington's diseases, ALS (amyotrophic lateral sclerosis), and other neurodegenerative disorders or symptoms derived from seizures, epilepsy, migraine headaches, diabetes, arteriosclerosis, and inflammatory diseases. Further, the present invention also relates to the method of producing above compounds.

BACKGROUND ART

In cellular disorders caused by advanced ischemia, the depletion of ATP, the fall in the pH in the cells, and the destruction of the mechanism for maintenance of the energy-dependent ion homeostasis inside and outside the cell cause the accumulation of a large amount of intracellular divalent Ca ions ($Ca^{2+}$). It is believed that the $Ca^{2+}$ overload causes functional disorders in the mitochondria and randomly activates various enzyme reactions and invites further $Ca^{2+}$ overload [F. B. Meyer: Brain Res. Rev., 14, 227 (1989); E. Boddeke et al.: Trends Pharmacol. Sci., 10, 397 (1989)]. On the other hand, while a small amount of active oxygen and free radicals such as superoxide anion radical ($O_2^-$), hydrogen peoxide ($H_2O_2$), hydroxy radical (OH.) and peroxynitrite ($ONOO^-$) produced along with the production of energy in the body and the metabolic process are effectively scavenged by enzymes such as SOD (superoxide dismutase) and catalase and natural antioxidants such as α-tocopherol ingested into the body, it is known that the excessive production of active oxygen/free radicals in ischemic diseases, neurodegenerative diseases, diabetes, arteriosclerosis, inflammatory diseases, or other diseases, imparts irreparable damage to the cell membrane through extensive lipid peroxidation or various radical reactions. Furthermore, arachidonic acid produced by the decomposition of the phospholipids in the cell membrane at that time is converted, through a peroxidation process (arachidonic acid cascade), to thromboxane $A_2$, which has a vascular constrictive and blood platlet aggregating actions, resulting in a cause of formation of thrombus, and therefore aggravates the cellular disorder. The two processes of the above $Ca^{2+}$ overload and excess production of active oxygen/free radicals, in cellular disorders caused by ischemia, act as mutually aggravating factors and are repeated in a vicious cycle which finally leads to cell death [J. M. McCall et al.: Ann. Rep. Med. Chem., 27, 31 (1992); C.-M. Andersson et al.: Advances in Drug Research, 28, 65. (1996)].

Therefore, pharmaceuticals which not only suppress cytotoxic $Ca^{2+}$ overload but also scavenge active oxygen/free radicals or suppress lipid peroxidation are considered to be those for the alleviation or treatment of various ischemic diseases, for example, cerebral infarction, cerebral edema, intracerebral hemorrhage, transient ischemic attack, subarachnoid hemorrhage, head trauma, after effects of brain surgery, after effects of cerebral arteriosclerosis, and other cerebrovascular disorders, or variant angina, unstable angina, myocardial infarction, cardiovascular system disorders accompanying surgery for revascularization by PTCA/PTCR/CABG etc., malignant arrhythmia and myocardial ischemia-reperfusion injury, and further disorders of transplanted organs at the time of organ transplants and temporary blockage of the blood flow in organs at the time of surgery, various neurodegenerative diseases, for example, Alzheimer's, Parkinson's and Huntington's diseases and ALS, and seizures, epilepsy, migraine headaches, and diabetes, arteriosclerosis, inflammatory diseases, etc.

As the arylpiperidine and arylpiperazine derivatives having an action of suppressing $Ca^{2+}$ overload, for example, there is known the compound described in International Patent Publication Nos. WO 96/22977 and WO 96/26924. No compound, however, is mentioned which has an action of suppressing lipid peroxidation as well as $Ca^{2+}$ overload.

DISCLOSURE OF INVENTION

Consequently, the objective of the present invention is to provide a compound having an action of suppressing cytotoxic $Ca^{2+}$ overload and lipid peroxidation and effective for the alleviation and treatment of symptoms due to ischemic diseases, neurodegenerative diseases and symptoms derived from seizures, epilepsy, migraine headaches, diabetes, arteriosclerosis, inflammatory diseases, and other diseases which is high in safety and suitable for use for preparations such as injections.

The present inventors synthesized and screened a series of compounds by evaluating the action of suppressing cytotoxic $Ca^{2+}$ overload and lipid peroxidation considered to cause ischemic cellular disorders and, as a result, found that arylpiperidinopropanol and arylpiperazinopropanol derivatives having the formula (I):

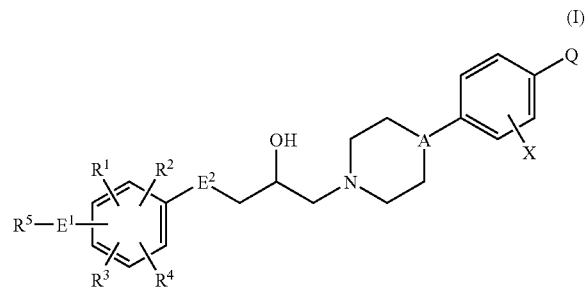

wherein $R^1$ to $R^4$ independently represent a hydrogen atom, a halogen atom, a hydroxy group, an alkoxy group, an optionally substituted alkyl group, an optionally substituted aryl group, or an optionally substituted aralkyl group, $R^5$ represents a hydrogen atom, an optionally substituted alkyl group, an optionally substituted aryl group, or an optionally substituted aralkyl group, $E^1$ represents an oxygen atom, a sulfur atom, or a group —$NR^6$, where $R^6$ represents a hydrogen atom, an optionally substituted alkyl group, an optionally substituted aryl group, or an optionally substituted aralkyl group, $E^2$ represents an oxygen atom, a sulfur atom, or a group —$NR^7$, where $R^7$ represents a hydrogen atom, an optionally substituted alkyl group, an optionally substituted aryl group, or an optionally substituted aralkyl group, A represents CH, C(OH), or a nitrogen atom, X represents a hydrogen atom, a halogen atom, an alkoxy group, or an optionally substituted alkyl group, and Q represents an optionally substituted phenyl group, an optionally substituted phenoxy group, an optionally substituted phenylmethyl group, or an optionally substituted cycloalkyloxy group, where when $E^1$ represents an oxygen atom or a sulfur atom, $E^2$ does not represent an oxygen atom or a sulfur atom, have not only an action in blocking non-L type $Ca^{2+}$ channels and $Na^+$ channels reported to be involved in the manifestation of $Ca^+$ overload [P. J. Pauwels et al.: Life Science, 48, 1881 (1991)], but also a powerful action in suppressing lipid peroxidation. Further, we confirmed that these compounds were effective in various pharmacological tests, with high in safety, and were suitable for pharmaceutical preparations and thereby completed the present invention.

BEST MODE FOR CARRYING OUT THE INVENTION

While the flunarizine being used as an agent for improvement of the brain circulation [J. P. Pauwels et al.: Life Science, 48, 1881 (1991); G. E. Billman: Eur. J. Pharmacol., 212, 231 (1992)] has the major defect in use of the side effect of manifestation of symptoms of Parkinson's disease due to the dopamine $D_2$ receptors blocking action, the compound having the general formula (I) of the present invention was found to have an extremely low affinity with respect to the cause of the side effects of flunarizine, the dopamine $D_2$ receptors.

In the present invention, as ischemic diseases, cerebral ischemic diseases, for example, cerebral infarction, intracerebral hemorrhage, transient ischemic attack, subarachnoid hemorrhage, head trauma, after effects of brain surgery, after effects of cerebral arteriosclerosis, and other cerebrovascular disorders, ischemic cardiac diseases, for example, variant angina, unstable angina, myocardial infarction, cardiovascular system disorders accompanying surgery for revascularization by PTCA/PTCR/CABG etc., malignant arrhythmia and other myocardial ischemia-reperfusion injury, and also disorders of transplanted organs at the time of organ transplants, and temporary blockage of the blood flow in organs at the time of surgery may be mentioned, and as neurodegenerative diseases, for example, Alzheimer's, Parkinson's and Huntington's diseases, ALS may be mentioned.

The compounds having the formula (I) of the present invention include compounds having the formulas (Ia), (Ib), and (Ic):

In the formula (Ia)

(Ia)

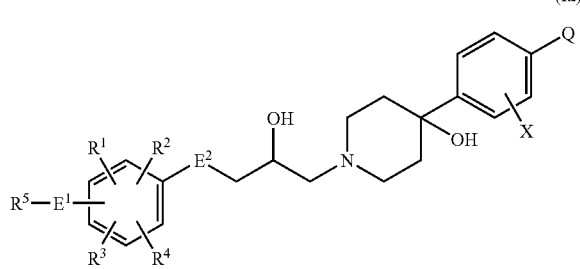

wherein, $R^1$ to $R^5$, $E^1$, $E^2$, X, and Q are the same as defined above, as the halogen atom indicated by $R^1$ to $R^4$, a fluorine atom, a chlorine atom, or a bromine atom may be mentioned, as the alkoxy group, a $C_1$ to $C_5$ linear or branched alkoxy group such as a methoxy group and an ethoxy group, etc. may be mentioned, as the optionally substituted alkyl group, a $C_1$ to $C_5$ linear or branched alkyl group optionally substituted with a halogen atom such as a methyl group, an ethyl group, a propyl group, or a trifluoromethyl group, etc. may be mentioned. As the aryl group of the optionally substituted aryl group, indicated by $R^1$ to $R^4$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and examples of the preferable substituent of the optionally substituted aryl group include a halogen atom such as a fluorine atom, a chlorine atom, or a bromine atom, a hydroxy group, a $C_1$ to $C_5$ linear or branched alkoxy group such as a methoxy group, or an ethoxy group, a $C_1$ to $C_5$ linear or branched alkyl group optionally substituted with a halogen atom such as a methyl group, an ethyl group, or a trifluoromethyl group, etc.

As the aralkyl group of the optionally substituted aralkyl group, indicated by $R^1$ to $R^4$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group, etc. may be mentioned.

As the optionally substituted alkyl group, indicated by $R^5$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group, indicated by $R^5$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group, indicated by $R^5$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

In the group —$NR^6$ of $E^1$ and the group —$NR^7$ of $E^7$, as the optionally substituted alkyl group indicated by $R^6$ or $R^7$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^6$ or $R^7$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group indicated by $R^6$ or $R^7$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

As the halogen atom indicated by X, a fluorine atom, a chlorine atom, or a bromine atom may be mentioned, as the alkoxy group, a $C_1$ to $C_5$ linear or branched alkoxy group such as a methoxy group or an ethoxy group may be mentioned, and as the optionally substituted alkyl group, a $C_1$ to $C_5$ linear or branched alkyl group optionally substituted with a halogen atom such as a methyl group, an ethyl group, a propyl group, or a trifluoromethyl group may be mentioned.

As the cycloalkyloxy group indicated by Q, a $C_4$ to $C_8$ cycloalkyloxy group such as a cyclobutyloxy group, a cyclopentyloxy group, a cyclohexyloxy group, or a cycloheptyloxy group.

As preferable substituents of the optionally substituted phenyl group, the optionally substituted phenoxy group, the optionally substituted phenylmethyl group or the optionally substituted cycloalkyloxy group indicated by Q, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the halogen atom of the $C_1$ to $C_5$ linear or branched alkyl group optionally substituted with a halogen atom, a fluorine atom, a chlorine atom, or a bromine atom may be mentioned.

In the formula (Ib)

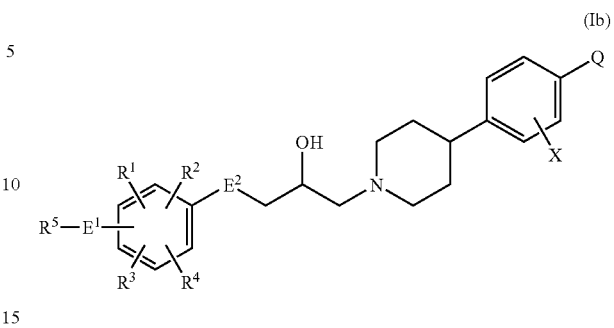

(Ib)

wherein, $R^1$ to $R^5$, $E^1$, $E^2$, X, and Q are the same as defined above, as the halogen atom indicated by $R^1$ to $R^4$, a fluorine atom, a chlorine atom, or a bromine atom may be mentioned, as the alkoxy group, a $C_1$ to $C_5$ linear or branched alkoxy group such as a methoxy group or an ethoxy group may be mentioned, and as the optionally substituted alkyl group, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group, indicated by $R^1$ to $R^4$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

As the aralkyl group of the optionally substituted aralkyl group, indicated by $R^1$ to $R^4$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, a $C_1$ to $C_5$ linear or branched alkyl group optionally substituted with a halogen atom such as a methyl group, an ethyl group, or a trifluoromethyl group, etc. may be mentioned.

As the optionally substituted alkyl group indicated by $R^5$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^5$, a $C_4$ to $C_{14}$ arl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group indicated by $R^5$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

In the group —$NR^6$ of $E^1$ and the group —$NR^7$ of $E^2$, as the optionally substituted alkyl group indicated by $R^6$ or $R^7$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^6$ or $R^7$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group indicated by $R^6$ or $R^7$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

As the halogen atom indicated by X, a fluorine atom, a chlorine atom, or a bromine atom maybe mentioned, as the alkoxy group, a $C_1$ to $C_5$ linear or branched alkoxy group such as a methoxy group or an ethoxy group may be mentioned, and as the optionally substituted alkyl group, a $C_1$ to $C_5$ linear or branched alkyl group optionally substituted with a halogen atom such as a methyl group, an ethyl group, a propyl group, or a trifluoromethyl group may be mentioned.

As the cycloalkyloxy group indicated by Q, a $C_4$ to $C_8$ cycloalkyloxy group such as a cyclobutyloxy group, a cyclopentyloxy group, a cyclohexyloxy group, or a cycloheptyloxy group may be mentioned.

As preferable substituents of the optionally substituted phenyl group, the optionally substituted phenoxy group, the optionally substituted phenylmethyl group or the optionally substituted cycloalkyloxy group indicated by Q, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the halogen atom of the $C_1$ to $C_5$ linear or branched alkyl group optionally substituted with a halogen atom, a fluorine atom, a chlorine atom, or a bromine atom may be mentioned.

In the formula (Ic)

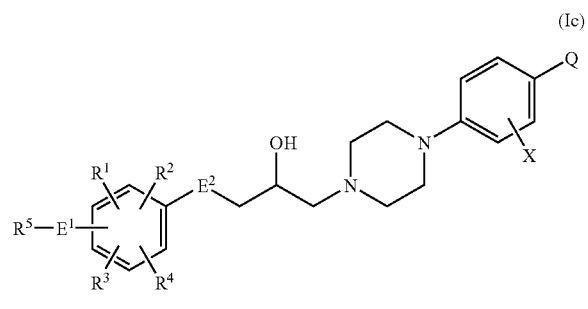

(Ic)

wherein, $R^1$ to $R^5$, $E^1$, $E^2$, X, and Q are the same as defined above, as the halogen atom indicated by $R^1$ to $R^4$, a fluorine atom, a chlorine atom, or a bromine atom may be mentioned, as the alkoxy group, a $C_1$ to $C_5$ linear or branched alkoxy group such as a methoxygroup or an ethoxy group may be mentioned, and as the optionally substituted alkyl group, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^1$ to $R^4$, a $C_4$ to $C_{14}$ aryl group which may contain one or more hetero atoms such as a.nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

As the aralkyl group of the optionally substituted aralkyl group indicated by $R^1$ to $R^4$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, a $C_1$ to $C_5$ linear or branched alkyl group optionally substituted with a halogen atom such as a methyl group, an ethyl group, or a trifluoromethyl group, etc. may be mentioned.

As the optionally substituted alkyl group indicated by $R^5$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^5$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group indicated by $R^1$, a $C_5$ to $C_{12}$ aralkyl group which may contain on its ring one or more hetero atoms such as a nitrogen atom or an oxygen atom may be mentioned, preferably a benzyl group, a phenylethyl group, a pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned.

In the group —$NR^6$ of $E^1$ and the group —$NR^7$ of $E^2$, as the optionally substituted alkyl group indicated by $R^6$ or $R^7$, a $C_1$ to $C_5$ linear or branched alkyl group optionally substituted with a halogen atom such as a methyl group, an ethyl group, a propyl group, or a trifluoromethyl group may be mentioned. As the aryl group of the optionally substituted aryl group indicated by $R^1$ or $R^7$, a $C_4$ to $C_{14}$ aryl group which may contain one or more hetero atoms such as a nitrogen atom or an oxygen atom may be mentioned, preferably a phenyl group, a naphthyl group, a pyridyl group, a quinolyl group, an isoquinolyl group, an indolyl group, etc. may be mentioned, and as preferable substituents of the optionally substituted aryl group, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the aralkyl group of the optionally substituted aralkyl group indicated by $R^6$ or $R^7$, a $C_5$ to $C_{12}$ aralkyl group which may contain on its ring one or more hetero atoms such as a nitrogen atom or an oxygen atom may be mentioned, preferably a benzyl group, a phenylethyl group, a 5 pyridylmethyl group, a pyridylethyl group, etc. may be mentioned, and as examples of the preferable substituent of the optionally substituted aralkyl group, a halogen atom such as a fluorine atom, a chlorine atom, or a bromine atom, a hydroxy group, a $C_1$ to $C_5$ linear or branched alkoxy group such as a methoxy group, an ethoxy group, a $C_1$ to $C_5$ linear or branched alkyl group optionally substituted with a halogen atom such as a methyl group, an ethyl group, or a trifluoromethyl group may be mentioned.

As the halogen atom indicated by X, a fluorine atom, a chlorine atom, or a bromine atom may be mentioned, as the alkoxy group, a $C_1$ to $C_5$ linear or branched alkoxy group such as a methoxy group or an ethoxy group may be mentioned, and as the optionally substituted alkyl group, a $C_1$ to $C_5$ linear or branched alkyl group optionally substituted with a halogen atom such as a methyl group, an ethyl group, a propyl group, or a trifluoromethyl group may be mentioned.

As the cycloalkyloxy group indicated by Q, a $C_4$ to $C_8$ cycloalkyloxy group such as a cyclobutyloxy group, a cyclopentyloxy group, a cyclohexyloxy group, or a cycloheptyloxy group may be mentioned.

As preferable substituents of the optionally substituted phenyl group, the optionally substituted phenoxy group, the optionally substituted phenylmethyl group or the optionally substituted cycloalkyloxy group indicated by Q, a halogen atom such as a fluorine atom, a chlorine atom, or a bromine atom, a hydroxy group, a $C_1$ to $C_5$ linear or branched alkoxy group such as a methoxy group, or an ethoxy group, and a $C_1$ to $C_5$ linear or branched alkyl group optionally substituted with a halogen atom such as a methyl group, an ethyl group, or a trifluoromethyl group may be mentioned. As the halogen atom of the $C_1$ to $C_5$ linear or branched alkyl group optionally substituted with a halogen atom, a fluorine atom, a chlorine atom, or a bromine atom may be mentioned.

Among the compounds represented by the formula (I), particularly preferable examples are listed below.

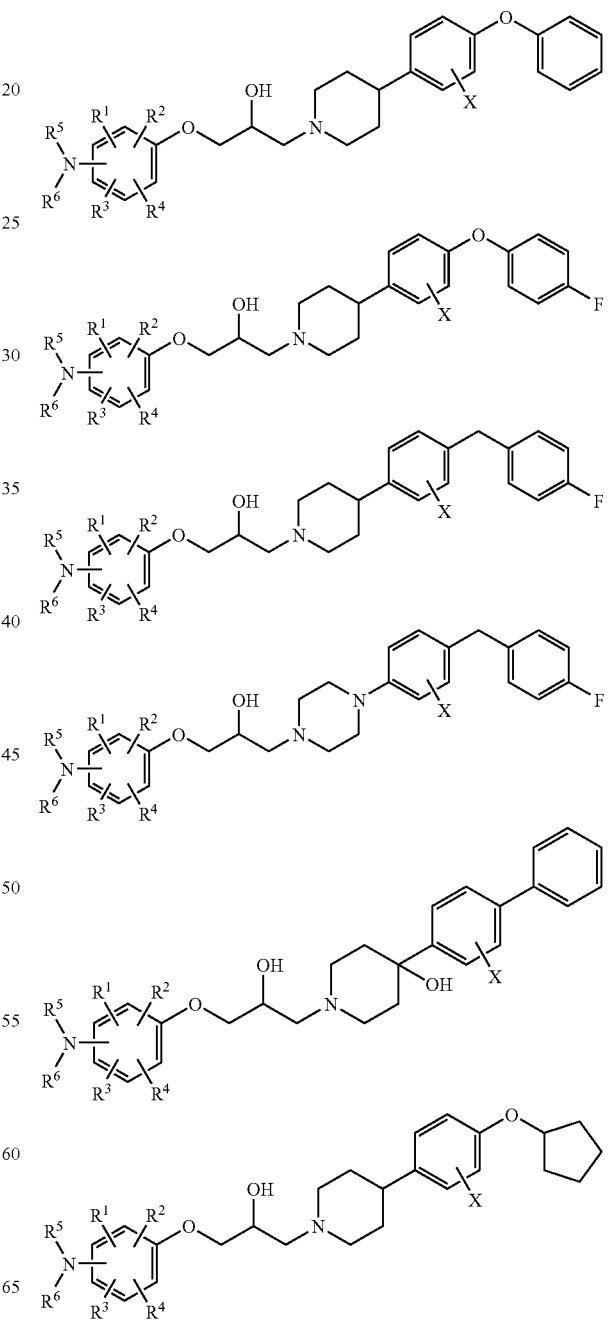

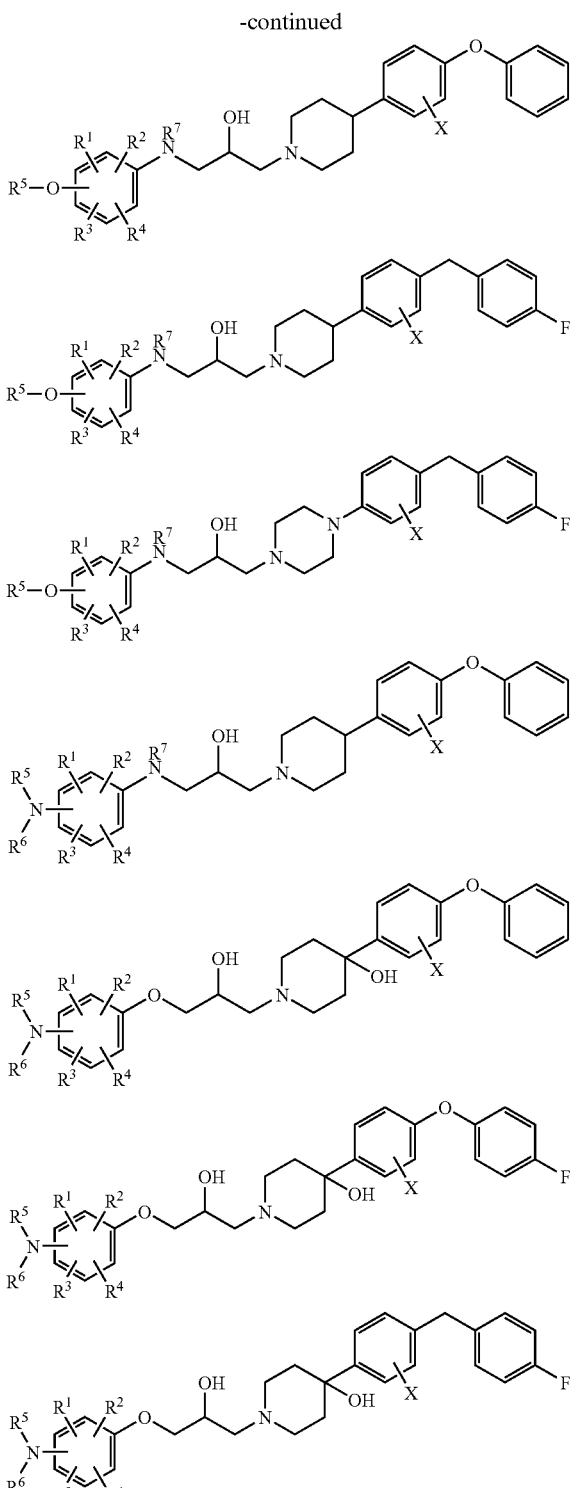

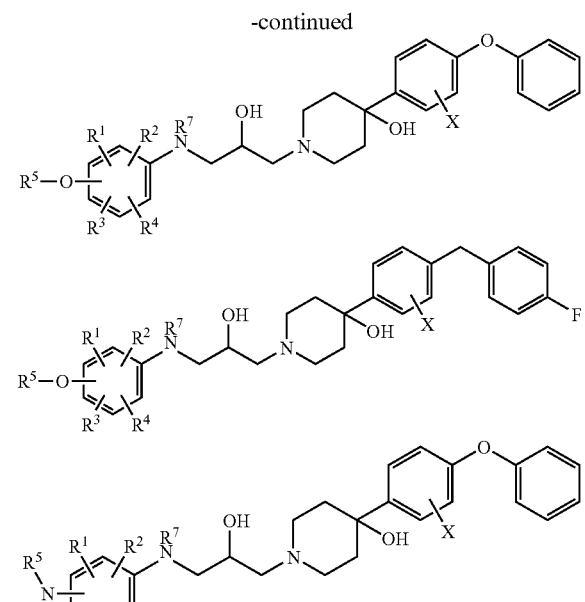

wherein, $R^1$ to $R^7$ and X are the same as defined above.

The compounds having the formula (I) of the present invention include isomers thereof. The present invention includes all of the individual isomers and mixtures thereof. That is, in the formula (I), there are structural isomers resulting from the difference in orientation of the substituent on the benzene ring and there are a pair of optical isomers for the asymmetric carbon atom to which the hydroxy group of the propanol moiety is bonded. The compounds of the present invention include all isomers resulting from combinations of these and mixtures of the same.

The compounds having the formula (I) according to the present invention can be synthesized in, for example, the following manner. These methods will be explained below.

The compound (Ia) wherein, in the formula (I), A is C(OH) can be obtained in the following way. That is, it is possible to obtain the compound (III) from the known starting material (II) (Step 1) and convert it to the compound (IV) (Step 2). Reaction of the compound (V) and the compound (VIa) or (VIb) gives the compound (VIIa), (VIIb) or (VIIc) (Step 3), which is then allowed to react with the compound (IV) to afford the compound (Ia) (Step 4).

The compound (Ib) wherein, in the formula (I), A is CH can be obtained by converting the compound (III) into the compound (X) (Step 5) followed by the reaction with the compound (VIIa) or (VIIb) (Step 6).

The compound (Ic) wherein, in the formula (I), A is a nitrogen atom can be obtained by converting the compound (XI) or (XIII) into the compound (XII) or (XII') (Step 7, 8) followed by the reaction with the compound (VIIa) or (VIIb) (Step 9).

Step 1

It is possible to synthesize the compound (III) from the known starting substance (II) by the following method.

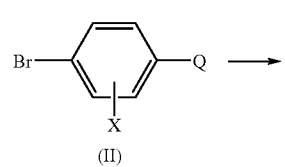

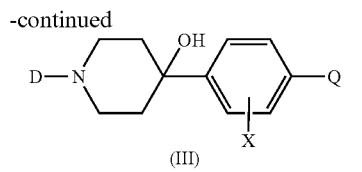

(III)

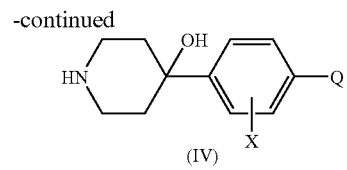

(IV)

wherein, X and Q are the same as defined above, D represents a benzyl group, a p-methoxybenzyl group, a benzyloxycarbonyl group, a p-methoxybenzyloxycarbonyl group, p-nitrobenzyloxycarbonyl group, a tert-butoxycarbonyl group, an ethoxycarbonyl group, or an acetyl group.

That is, an aryl bromide derivative (II) is converted by conventional method to the corresponding aryl Grignard reagent or aryl lithium reagent, then reacted in tetrahydrofuran, diethyl ether, ethylene glycol dimethyl ether, toluene, or another solvent not participating in the reaction, at −100° C. to 50° C., preferably −78° C. to room temperature, with 1 to 1.5 equivalents of the known starting material N-benzyl-4-piperidone, N-(p-methoxybenzyl)-4-piperidone, N-benzyloxycarbonyl-4-piperidone, N-(p-methoxybenzyloxycarbonyl)-4-piperidone, N-(p-nitrobenzyloxycarbonyl)-4-piperidone, N-tert-butoxycarbonyl-4-piperidone, N-ethoxycarbonyl-4-piperidone, or N-acetyl-4-piperidone for 1 to 6 hours, whereby a compound having the formula (III) is obtained.

The starting substance (II) used in the present reaction is a known compound or alternatively can be synthesized by known methods [L. Martin et al.: J. Med. Chem., 22, 1347 (1979); J.-P. Genet et al.: Tetrahedron Lett., 37, 3857 (1996); G. Faye Crr et al.: J. Med. Chem., 40, 1179 (1997)]. For example, 4-bromodiphenyl ether, 4-bromophenyl ether, 4-bromo-4'-fluorodiphenyl ether, 4-bromo-3'-fluorodiphenyl ether, 4-bromo-2'-fluorodiphenyl ether, 4-bromodiphenyl methane, 4-bromo-4'-fluorodiphenyl methane, 4-bromo-4'-chlorodiphenyl methane, 4-bromo-4'-methoxydiphenyl methane, 4-bromo-4'-trifluoromethyldiphenyl methane, 4-bromobiphenyl, 4-bromo-2-fluorobiphenyl, 4-bromo-4'-fluorobiphenyl, 4-bromo-4'-methoxybiphenyl, 4-bromo-4'-methylbiphenyl, 4-bromo-4'-trifluoromethylbiphenyl, 4,4,-dibromobiphenyl, 4-bromophenylcyclopentyl ether, 4-bromophenylcyclohexyl ether, etc. can be used.

As the conditions for preparing the Grignard reagent and the organolithium reagent, it is possible to use the various methods described in the "Compendium for Organic Synthesis" (Wiley-Interscience: A Division of John Wiley & Sons) etc.

The compound obtained in the above reaction can be used as is for the next step or, if necessary, can be used after purification by a conventional method such as recrystallization or column chromatography.

Step 2

It is possible to synthesize the compound (IV) from the compound (III) obtained in Step 1.

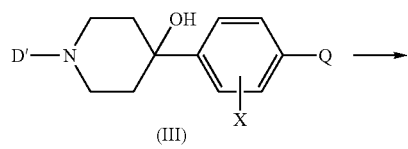

(III)

wherein, X and Q are the same as defined above, D' represents a benzyl group, a p-methoxybenzyl group, a benzyloxycarbonyl group, a p-methoxybenzyloxycarbonyl group, or a p-nitrobenzyloxycarbonyl group.

The compound (III) obtained in Step 1 can be converted to the compound having the formula (IV) by hydrogenation in ethyl acetate, methanol, ethanol, isopropyl alcohol, or another solvent not participating in the reaction, in the presence of a catalytic amount of palladium carbon, palladium hydroxide, platinum, etc. at a pressure to 6 atmospheres. Further, in the reaction, if necessary, acetic acid, hydrochloric acid, or other acid may be added.

Step 3

The compound (V) can be reacted with the compound (VIa) or (VIb) to synthesize the compound (VIIa), (VIIb) or (VIIc).

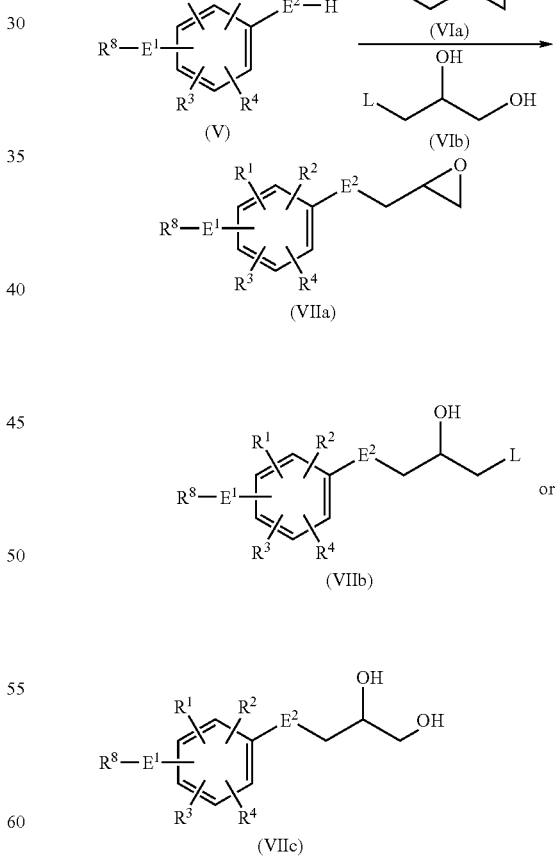

wherein, $R^1$ to $R^4$, $E^1$ and $E^2$ are the same as defined above, $R^8$ represents an optionally substituted alkyl group, an optionally substituted aryl group, an optionally substituted aralkyl group, a benzyl group, a p-methoxybenzyl group, a benzyloxycarbonyl group, a p-methoxybenzyloxycarbonyl group, a p-nitrobenzyloxycarbonyl group, a tert-butoxycarbonyl group, an ethoxycarbonyl group, an acetyl group, or a formyl group, and L represents a group which can be easily exchanged with an amino group.

That is, the compound (V) is stirred in benzene, toluene, tetrahydrofuran, dioxane, dimethylformamide, dimethylsulfoxide, acetonitrile, acetone, methanol, ethanol, isopropyl alcohol, tert-butyl alcohol, ethylene glycol or another solvent not participating in the reaction and, if necessary, in the presence of an organic base such as triethylamine, diisopropylethylamine, or pyridine or an inorganic base such as sodium, sodium hydride, potassium, potassium hydride, sodium methoxide, sodium ethoxide, potassium ethoxide, potassium tert-butoxide, sodium carbonate, potassium carbonate, cesium carbonate, cesium fluoride, sodium hydrogencarbonate, or potassium hydrogencarbonate at −20° C. to 150° C., preferably 0° C. to 100° C., with 1.0 to 1.5 equivalents of the compound (VIa) or (VIb), whereby the compound (VIIa), (VIIb) or (VIIc) is obtained. Further, in this reaction, if necessary, a plurality of organic bases and inorganic bases may be combined for use or sodium iodide or tetrabutylammonium iodide etc. may be added. L is a leaving group easily exchangeable with an amino group. A halogen atom such as a chlorine atom, a bromine atom, or an iodine atom, an alkylsulfonyloxy group such as a methanesulfonyloxy group, an arylsulfonyloxy group such as a p-toluenesulfonyloxy group or a 3-nitrobenzenesulfonyloxy group, etc. may be exemplified.

As the compounds (V), (VIa) and (VIb) used in this reaction, commercially available or known compounds or alternatively those which can be synthesized by known methods can be used. As the compound (V), 4-(tert-butoxycarbonylamino)-phenol, 4-(benzyloxycarbonylamino)-phenol, 4-(p-methoxybenzyloxycarbonylamino)-phenol, 4-(p-nitrobenzyloxycarbonylamino)-phenol, 4-(tert-butoxycarbonylamino)-2,3,5-trimethylphenol, 4-(benzyloxycarbonylamino)-2,3,5-trimethylphenol, 4-(p-methoxybenzyloxycarbonylamino)-2,3,5-trimethylphenol, 4-(p-nitrobenzyloxycarbonylamino)-2,3,5-trimethylphenol, 4-(tert-butoxycarbonylamino)-2-chloro-3,5,6-trimethylphenol, 4-(benzyloxycarbonylamino)-2-chloro-3,5,6-trimethylphenol, 4-(p-methoxybenzyloxycarbonylamino)-2-chloro-3,5,6-trimethylphenol, 4-(p-nitrobenzyloxycarbonylamino)-2-chloro-3,5,6-trimethylphenol, 4-(tert-butoxycarbonylamino)-2,3,6-trimethylphenol, 4-(benzyloxycarbonylamino)-2,3,6-trimethylphenol, 4-(p-methoxybenzyloxycarbonylamino)-2,3,6-trimethylphenol, 4-(p-nitrobenzyloxycarbonylamino)-2,3,6-trimethylphenol, 4-(tert-butoxycarbonylamino)-2,3-dimethylphenol, 4-(benzyloxycarbonylamino)-2,3-dimethylphenol, 4-(p-methoxybenzyloxycarbonylamino)-2,3-dimethylphenol, 4-(p-nitrobenzyloxycarbonylamino)-2,3-dimethylphenol, 4-(tert-butoxycarbonylamino)-2,5-dimethylphenol, 4-(benzyloxycarbonylamino)-2,5-dimethylphenol, 4-(p-methoxybenzyloxycarbonylamino)-2,5-dimethylphenol, 4-(p-nitrobenzyloxycarbonylamino)-2,5-dimethylphenol, 2-(tert-butoxycarbonylamino)-4,6-dimethylphenol, 2-(benzyloxycarbonylamino)-4,6-dimethylphenol, 2-(p-methoxybenzyloxycarbonylamino)-4,6-dimethylphenol, 2-(p-nitrobenzyloxycarbonylamino)-4,6-dimethylphenol, 5-(tert-butoxycarbonylamino)-2-methoxyphenol, 5-(benzyloxycarbonylamino)-2-methoxyphenol, 5-(p-methoxybenzyloxycarbonylamino)-2-methoxyphenol, 5-(p-nitrobenzyloxycarbonylamino)-2-methoxyphenol, 5-(tert-butoxycarbonylamino)-4-chloro-2-methoxyphenol, 5-(benzyloxycarbonylamino)-4-chloro-2-methoxyphenol, 5-(p-methoxybenzyloxycarbonylamino)-4-chloro-2-methoxyphenol, 5-(p-nitrobenzyloxycarbonylamino)-4-chloro-2-methoxyphenol, 4-(tert-butoxycarbonylamino)-2,6-dichlorophenol, 4-(benzyloxycarbonylamino)-2,6-dichlorophenol, 4-(p-methoxybenzyloxycarbonylamino)-2,6-dichlorophenol, 4-(p-nitrobenzyloxycarbonylamino)-2,6-dichlorophenol, 4-(tert-butoxycarbonylamino)-2,3,4,6-tetramethylaniline, 4-(benzyloxycarbonylamino)-2,3,4,6-tetramethylaniline, 4-(p-methoxybenzyloxycarbonylamino)-2,3,4,6-tetramethylaniline, 4-(p-nitrobenzyloxycarbonylamino)-2,3,4,6-tetramethylaniline, 4-methoxy-2-methylaniline, etc. may be exemplified.

As the compound (VIa), epibromohydrin, epichlorohydrin, (R)-epichlorohydrin, (S)-epichlorohydrin, glycidyltosylate, (R)-glycidyltosylate, (S)-glycidyltosylate, (R)-glycidyl 3-nitrobenzenesulfonate, (S)-glycidyl 3-nitrobenzenesulfonate, (R)-glycidyl 4-nitrobenzoate, (S)-glycidyl 4-nitrobenzoate, glycidyl trimethylammonium chloride, etc. may be exemplified.

As the compound (VIb), 3-bromo-1,2-propanediol, 3-chloro-1,2-propanediol, (R)-3-chloro-1,2-propanediol, (S)-3-chloro-1,2-propanediol, etc. may be exemplified.

Step 4

The compound (IV) obtained in Step 2 and the compound (VIIa), (VIIb) or (VIIc) obtained in Step 3 can be reacted to synthesize the compound (Ia) where in the formula (I), A is C(OH).

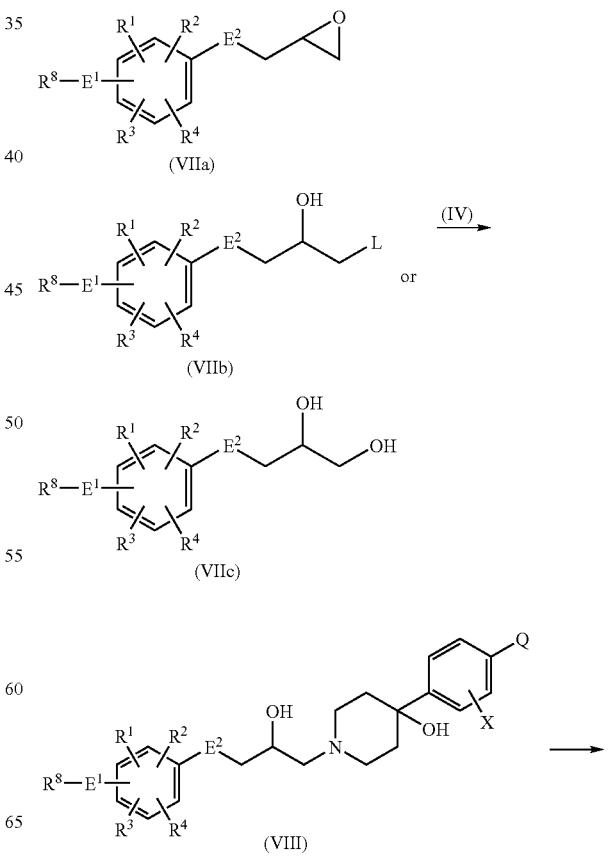

-continued

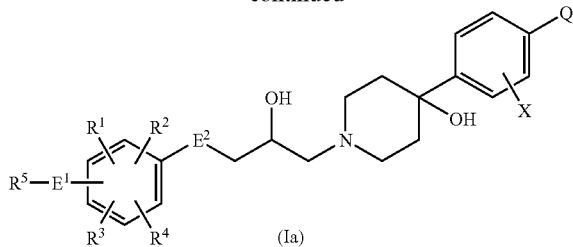

(Ia)

wherein $R^1$ to $R^5$, $R^8$, $E^1$, $E^2$, X, Q, and L are the same as defined above.

The compound (VIIa) or (VIIb) obtained at Step 3 is reacted in benzene, toluene, tetrahydrofuran, diethyl ether, ethylene glycol dimethylether, dioxane, dimethylformamide, dimethylsulfoxide, acetonitrile, methanol, ethanol, isopropyl alcohol, tert-butyl alcohol, ethylene glycol, or another solvent not participating in the reaction at room temperature to 200° C., preferably 50° C. to 150° C., with 0.9 to 1.5 equivalents of the compound (IV) obtained in Step 2 for 1 to 24 hours, whereby the compound (VIII) can be obtained.

Further, the compound (VIIc) obtained in Step 3 is converted to the compound (VIIa) or (VIIb) by known methods [e.g., K. B. Sharpless et al.: Tetrahedron, 48, 10515 (1992); S. Takano et al.: Synthesis, 503 (1985); A. K. Ghosh et al.: J. Chem. Soc., Chem. Commun., 273 (1992); M. K. Ellis et al.: Organic Synthesis, Collective Volume 7, 356 (1990); S. Takano et al.: Heterocycles, 16, 381 (1981); A. K. M. Anisuzzaman et al.: J. Chem. Soc., C, 1021 (1967)], followed by carrying out the same reactions with the compound (IV) to give the compound (VIII).

Further, in this reaction, if necessary, an organic base such as triethylamine, diisopropylethylamine, or pyridine, an inorganic base such as sodium carbonate, potassium carbonate, cesium carbonate, cesium fluoride, sodium hydrogencarbonate, or potassium hydrogencarbonate, or a metal salt such as sodium iodide, tetrabutylammonium iodide, lithium carbonate, lithium chloride, zinc bromide, or magnesium bromide may be added alone or in combination.

Further, by hydrogenation of the compound (VIII) where $R^8$ is a benzyl group, a p-methoxybenzyl group, a benzyloxycarbonyl group, a p-methoxybenzyloxycarbonyl group, or a p-nitrobenzyloxycarbonyl group or by an acid treatment with hydrochloric acid, sulfuric acid, nitric acid, hydrobromic acid, trifluoroacetic acid, methanesulfonic acid, trifluoromethanesulfonic acid, etc. of the compound (VIII) where $R^8$ is a tert-butoxycarbonyl group, a p-methoxybenzyloxycarbonyl group, an ethoxycarbonyl group, an acetyl group, or a formyl group, it is possible to synthesize the compound (Ia) wherein, in the formula (I), A is C(OH).

The compounds obtained by the above reactions can be used as they are for the next step or, if necessary, can be used after purification by a conventional method such as recrystallization or column chromatography.

Further, the reactions in Step 3 and Step 4 can be carried out successively in one-pot without isolating the compounds obtained by the each reaction.

Step 5

The compound (X) can be synthesized from the compound (III) obtained in Step 1.

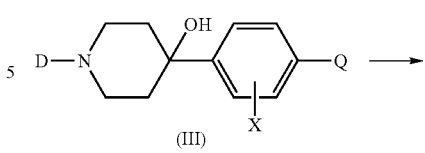

(III)

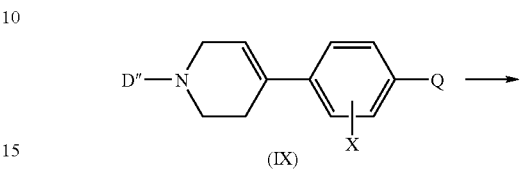

(IX)

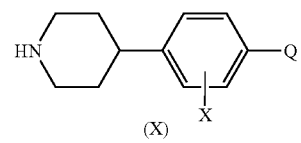

(X)

wherein, X, Q, and D are the same as defined above, D" represents a hydrogen atom, a benzyl group, a p-methoxybenzyl group, a benzyloxycarbonyl group, a p-methoxybenzyloxycarbonyl group, or a p-nitrobenzyloxycarbonyl group.

The compound (III) obtained in Step 1 is treated under non-solvent conditions or in a solvent not participating in the reaction, for example, tetrahydrofuran, diethyl ether, ethylene glycoldimethyl ether, benzene, toluene, methylene chloride, chloroform, carbon tetrachloride, water, methanol, or ethanol at −20° C. to 150° C., preferably 0° C. to 80° C., with 1 to 20 equivalents of an organic acid such as acetic acid, trifluoroacetic acid, methanesulfonic acid, or trifluoromethanesulfonic acid or an inorganic acid such as hydrochloric acid, sulfuric acid, or nitric acid for 1 to 12 hours or the compound (III) is treated in a solvent not participating in the reaction, for example, benzene, toluene, methylene chloride, chloroform, or carbon tetrachloride, if necessary, in the presence of triethylamine, pyridine, or diisopropylethylamine, or other bases at −20° C. to 150° C., preferably 0° C. to 100° C., with 1 to 5 equivalents of thionyl chloride, methanesulfonyl chloride, trifluoromethanesulfonyl chloride, trifluoromethanesulfonate anhydride, p-toluenesulfonyl chloride, phosphorus oxychloride, or other acid chloride derivatives for 1 to 6 hours, and the subsequent acid treatment similar to the above is repeated, whereby the compound (IX) is obtained. Next, the compound (IX) is processed by a similar method as in Step 2, to give the compound having the formula (X).

The compounds obtained by the above reactions can be used as they are for the next step, but if necessary can also be used after purification by a conventional method such as recrystallization or column chromatography.

Step 6

Starting with the compound (VIIa), (VIIb) or (VIIc) obtained in Step 3 and the compound (X) obtained in Step 5, it is possible to synthesize the compound (Ib) wherein, in the formula (I), A is CH, by a similar method as in Step 4.

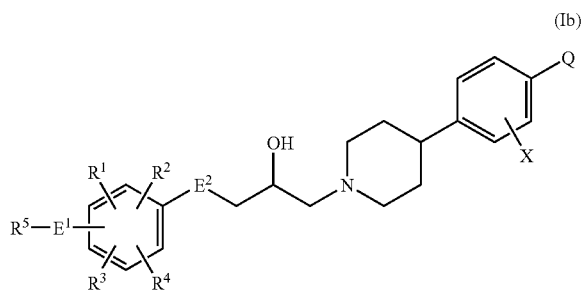

(Ib)

wherein, $R^1$ to $R^5$, $E^1$, $E^2$, X, and Q are the same as defined above.

Step 7

It is possible to synthesize the compound (XII) from compound (XI).

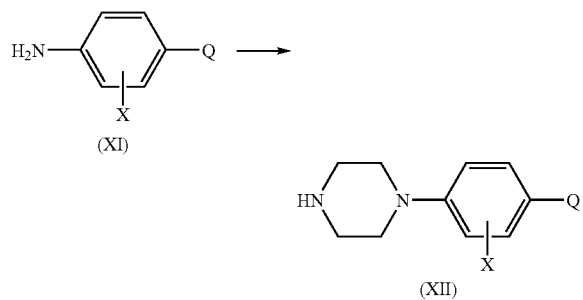

wherein, X and Q are the same as defined above.

That is, an aniline derivative having the general formula (XI) is reacted under non-solvent conditions or in a solvent not participating in the reaction, such as n-butanol, tert-butyl alcohol, ethylene glycol, diglyme, dimethylformamide or dimethylsulfoxide at 50 to 300° C., preferably 150 to 250° C., with 1 to 1.5 equivalents of known bis-2-chloroethylamine hydrochloride for 1 to 12 hours, whereby the compound having the general formula (XII) is obtained.

The starting substance (XI) used in this reaction may be a commercially available or a known compound [K. Suzuki et al.: J. Org. Chem., 26, 2239 (1961)] or alternatively can be synthesized by a known method as for example disclosed in Japanese Examined Patent Publication (Kokoku) No. 6-25191. For example, 4-phenoxyaniline, 4-(4-fluorophenoxy)aniline, 4-benzylaniline, 4-(4-fluorophenyl)methylaniline, 4-(4-methoxyphenyl)methylaniline, 4-(4-chlorophenyl)methylaniline, 4-(4-trifluoromethylphenyl)methylaniline, 4-benzyl-3-methoxyaniline, 4-(4-fluorophenyl)methyl-3-methoxyaniline, 3-fluoro-4-(4-fluorophenyl)methylaniline, 3-fluoro-4-(4-methoxyphenyl)methylaniline, 3-methoxy-4-(4-methoxyphenyl)methylaniline, 4-aminobiphenyl, etc. may be mentioned.

Further, in this reaction, if necessary, an inorganic base such as sodium hydrogencarbonate, potassium hydrogencarbonate, sodium carbonate, or potassium carbonate may be added.

The compound obtained in the above reaction may be used as is for the next step, but if necessary may also be used after purification by a conventional method, such as recrystallization or column chromatography.

Step 8

The compound (XII') among the compound represented by the formula (XII), wherein Q is an optionally substituted phenylmethyl group can be synthesized from the compound (XIII) and compound (XIV).

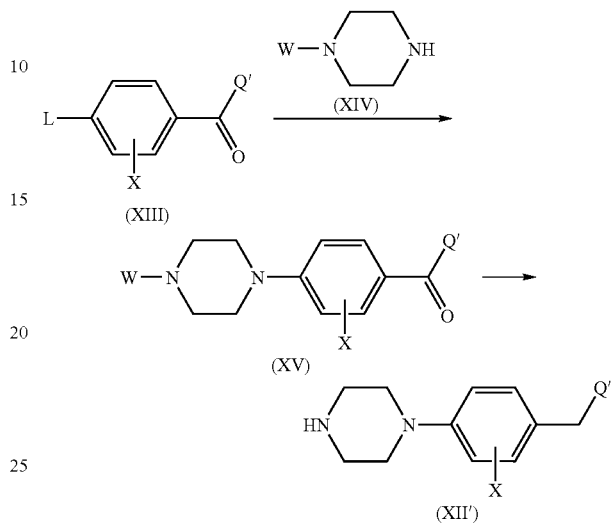

wherein L and X are the same as defined above, Q' represents an optionally substituted phenyl group, and W represents a hydrogen atom, a benzyl group, a p-methoxybenzyl group, a benzyloxycarbonyl group, a p-methoxybenzyloxycarbonyl group, a p-nitrobenzyloxycarbonyl group, a tert-butoxycarbonyl group, an ethoxycarbonyl group or an acetyl group.

That is, a benzophenone derivative (XIII) is reacted with 1 to 20 equivalents of piperazine derivative (XIV) at 50-300° C. for 1 hour to 20 days under non-solvent conditions, or in a solvent not participating in the reaction, such as methanol, ethanol, n-butanol, tert-butyl alcohol, acetonitrile, nitromethane, dioxane, tetrahydrofuran, dimethylacetamide, dimethylsulfoxide, N-methyl-2-pyrrolidone, to give the compound (XV). In this reaction, if necessary, an organic base such as triethylamine, diisopropylethylamine, pyridine, or an inorganic base such as sodium, sodium hydride, potassium hydride, sodium ethoxide, potassium tert-butoxide, sodium carbonate, potassium carbonate, cesium carbonate., cesium fluoride, sodium hydrogenbicarbonate, potassium hydrogenbicarbonate, or any combination thereof may be added.

Then, the compound (XV) is treated in the same way as in Step 2, or is treated with 1 to 20 equivalents of sodium, triethylsilane or borane in a solvent not participating in the reaction, such as ether, tetrahydrofuran, dioxane, 1,2-dimethoxyethane, methylene chloride, chloroform, benzene, toluene, acetic acid, trifluoroacetic acid, methanesulfonic acid, trifluoromethanesulfonic acid, liquid ammonia, methanol, ethanol, 2-propanol, to give the compound (XII'). If necessary, in this reaction, a catalytic amount of acid such as hydrochloric acid, sulfuric acid, hydrobromic acid, nitric acid, boran trifluoride may be added. Furthermore, the compound which W represents an ethoxycarbonyl group or an acetyl group in the general formula (XV) can be converted into the compound (XII') by the above mentioned procedure followed by stirring at 50-200° C. for 1 hour to 3 days in an aqueous acidic solution such as acetic acid, acetic acid/hydrochloric acid, hydrobromic acid, sulfuric acid.

As the compound (XIII) usable in the present reaction, for example, 2,4-difluorobenzophenone, 2,4'-difluorobenzophenone, 3,4-difluorobenzophenone, 4,4'-difluorobenzophenone, 4-bromo-4'-fluorobenzophenone, 4-chloro-4'-fluorobenzophenone, 4-fluoro-4'-methoxybenzophenone, 4'-bromo-4'-methoxybenzophenone, 4-fluoro-4'-methylbenzophenone, 4-bromo-4'-methylbenzophenone may be mentioned. As the compound (XIV), for example, piperazine, 1-benzylpiperazine, 1-(p-methoxybenzyl)piperazine, 1-benzyloxycarbonylpiperazine, 1-(p-methoxybenzyloxycarbonyl)piperazine, 1-(p-nitrobenzyloxycarbonyl)piperazine, 1-(tert-butoxycarbonyl)piperazine, 1-ethoxycarbonylpiperazine, 1-acetylpiperazine may be mentioned.

The compound obtained in the above each reaction can be used as is for the next step or, if necessary, can be used after purification by a conventional method such as recrystallization or column chromatography.

Step 9

Starting with the compound (VIIa), (VIIb) or (VIIc) obtained in Step 3 and the compound (XII) obtained in Step 7 or the compound (XII') obtained in Step 8, it is possible to synthesize the compound (Ic) where, in the general formula (I), A is a nitrogen atom, by a similar method as in Step 4.

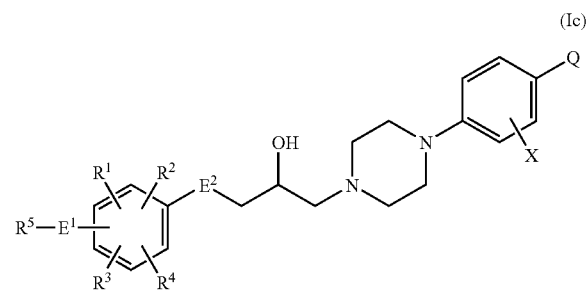

(Ic)

wherein, $R^1$ to $R^5$, $E^1$, $E^2$, X, and Q are the same as defined above.

Individual isomers included in the compounds of general formula (I) of the present invention can be separated by a conventional method, for example, recrystallization, column chromatography, thin layer chromatography, high performance liquid chromatography, or a similar method using optically active reagents.

The compound having the general formula (I) of the present invention can be dissolved in a suitable organic solvent, for example, methanol, ethanol, isopropyl alcohol, tert-butyl alcohol, ether, tetrahydrofuran, methylene chloride, chloroform, benzene, toluene, and treated with an inorganic acid or an organic acid to afford the corresponding salt. As the inorganic acid used here, hydrochloric acid, hydrobromic acid, sulfuric acid, nitric acid, phosphoric acid, periodic acid, etc. and as the organic acid, formic acid, acetic acid, butyric acid, oxalic acid, malonic acid, propionic acid, valeric acid, succinic acid, fumaric acid, maleic acid, tartaric acid, citric acid, malic acid, benzoic acid, p-toluenesulfonic acid, methanesulfonic acid, ethanesulfonic acid, 2-hydroxyethanesulfonic acid, trifluoromethanesulfonic acid, benzenesulfonic acid, etc. may be mentioned.

It should be noted that the salts comprising 1 to 3 molecules of the acid can be selectively prepared by adjusting the amount of the above-mentioned inorganic acid or organic acid used between 1 to 3 equivalents depending upon the number of the basic nitrogen atom present in the compound (I).

The crude crystal of the resultant salt can be purified by recrystallization thereof from a solvent such as water, methanol, ethanol, isopropyl alcohol, tert-butyl alcohol, ether, diisopropyl ether, tetrahydrofuran, methylene chloride, chloroform, dichloroethane, hexane, cyclohexane, petroleum ether, acetonitrile, acetic acid, ethyl acetate or any mixture thereof. In this purification step, a small amount of an inorganic or organic acid corresponding to the salt may be added.

The compound having the formula (I) of the present invention is low in toxicity and can be used alone by itself, or if desired, can be converted into a pharmaceutical preparation with other normal pharmaceutically allowable known and generally used carriers designed for the alleviation and treatment of symptoms due to ischemic diseases and neurodegenerative diseases, symptoms derived from seizures, epilepsy, and migraine headaches and symptoms arising from diabetes, arteriosclerosis, and inflammatory diseases. For example, the effective ingredient can be administered orally or nonorally by itself or a capsule, tablet, injection, or a suitable preparation together with usually used excipients. For example, capsules can be prepared by mixing the original powder with an excipient such as lactose, starch or its derivative, or a cellulose derivative and filling the resultant mixture into gelatin capsules. Further, tablets can be prepared by kneading in, in addition to the above excipient, sodium carboxymethylcellulose, alginic acid, arabic gum or other binders and water, if necessary, granulating the same, then further adding talc, stearic acid, or other lubricants and preparing the final form using a normal compression tabletizer. At the time of non-oral administration by injection, the effective ingredient is dissolved with a solubilizer in sterilized distilled water or sterilized saline and sealed into an ampule to make the injection preparation. If necessary, it is also possible to add a stabilizer, buffer, etc.

The dosage of the pharmaceutical composition of the present invention differs depending on various factors, for example, the symptoms, the gravity of symptoms, the age, the complications of the patient to be treated, etc. and further depending on the route of administration, the form of the preparation, the frequency of administration, etc. In the case of oral administration, as the effective ingredient, normally 0.1 to 1000 mg/day/person, preferably 1 to 500 mg/day/person, while in the case of non-oral administration, 1/100 to ½ the amount of the case of oral administration can be administered. The amounts of dosages may be suitably adjusted according to the age, symptoms, etc. of the patient.

EXAMPLES

The present invention will now be explained in further detail with reference to the Reference Examples and Examples, but the scope of the present invention is by no means limited to these Examples.

Reference Example 1

Synthesis of N-tert-butoxycarbonyl-4-[4-(4-fluorophenoxy)phenyl]-4-piperidinol (1) (Note: Compound No. 1 in Table 1 (same below))

To a 10 ml of tetrahydrofuran solution of 4.08 g of N-tert-butoxycarbonyl-4-piperidone, a 30 ml of (4-fluorophenoxy)phenyl magnesium bromide prepared from 4-bromo-4'-fluorodiphenylether (0.6 mol/l tetrahydrofuran solution) was dropwise added under ice cooling and the resultant mixture was stirred for 1 hour. To the reaction mixture, a 30 ml of saturated aqueous ammonium chloride solution was added and the product was extracted with ether. The extract was washed with saturated saline, dried, filtered, then concentrated under reduced pressure to give a residue, which was then purified by silica gel column chromatography (hexane:ethyl acetate=5:1) to give the above-referenced compound (1) in an amount of 2.45 g (yield 42%).

Reference Example 2

Synthesis of N-benzyl-4-(3-fluoro-4-phenyl)phenyl-4-piperidinol (2)

The same procedure was followed as in Reference Example 1 using N-benzyl-4-piperidone and 4-bromo-2-fluorobiphenyl to produce the above.

Reference Example 3

Synthesis of N-tert-butoxycarbonyl-4-(4-cyclopentyloxy)phenyl-4-piperidinol (3)

The same procedure was followed as in Reference Example 1 using 4-bromophenoxycyclopentane to produce the above.

Reference Example 4

Synthesis of 4-[4-(4-fluorophenoxy)phenyl]-1,2,3,6-tetrahydropyridine (4)

To a 15 ml methylene chloride solution of 2.4 g of the compound (I) synthesized in Reference Example 1, a 5 ml of trifluoroacetic acid was dropwise added under ice cooling. The resultant mixture was stirred at room temperature overnight, then was adjusted by 10% aqueous sodium hydroxide solution to pH=9 to 10 and extracted with ether. The extract was dried, filtered, then concentrated under reduced pressure to give a residue, which was then purified by silica gel column chromatography (chloroform:methanol=10:1) to give the above-referenced compound (4) in an amount of 1.62 g (yield 97%).

Reference Example 5

Synthesis of 4-(4-cyclopentyloxy)phenyl-1,2,3,6-tetrahydropyridine (5)

The compound (3) synthesized in Reference Example 3 was used to produce the above in the same way as in Reference Example 4.

Reference Example 6

Synthesis of 4-(4-cyclopentyloxy)phenylpiperidine (7)

The compound (5) synthesized in Reference Example 5 was used to produce the above in the same way as in the later Example 1.

Reference Example 7

Synthesis of 4-(4-phenoxyphenyl)piperidine

Step A
To an 100 ml tetrahydrofuran solution of 3.5 g of N-tert-butoxycarbonyl-4-piperidone, a 35 ml of 4-phenoxyphenyl magnesium bromide prepared from 4-bromodiphenyl ether (0.6 mol/l tetrahydrofuran solution) was dropwise added under ice cooling and the resultant mixture was stirred for 1 hour. To the reaction mixture was added a 30 ml of saturated aqueous ammonium chloride solution. The product was extracted with ether. The extract was washed with saturated saline, dried, filtered, then concentrated under reduced pressure to give a residue, which was then purified by silica gel column chromatography (hexane:ethyl acetate=3:1) to give N-tert-butoxycarbonyl-4-(4-phenoxyphenyl)-4-piperidinol in an amount of 2.92 g (yield 45%).

Step B
To a 3 ml of methylene chloride solution of 772 mg of N-tert-butoxycarbonyl-4-(4-phenoxyphenyl)-4-piperidinol synthesized in Step A, a 3 ml of trifluoroacetic acid was dropwise added under ice cooling. The resultant mixture was stirred at room temperature for 2 hours, then adjusted by 10% aqueous sodium hydroxide solution to pH=9 to 10 and extracted with ether. The extract was dried, filtered, then concentrated under reduced pressure to give a residue, which was then recrystallized from ether/methylene chloride to give 4-(4-phenoxyphenyl)-1,2,3,6-tetrahydropyridine in an amount of 250 mg (yield 47%).

Step C
To an 100 ml methanol solution of 3.51 g of the 4-(4-phenoxyphenyl)-1,2,3,6-tetrahydropyridine synthesized in Step B was added a 200 mg of palladium carbon and 1 ml of acetic acid. The resultant mixture was hydrogenated under atmospheric pressure at room temperature. After completion of the reaction, the insolubles were filtered off and the filtrate was concentrated under reduced pressure. The residue obtained was dissolved in methylene chloride, adjusted by 10% aqueous sodium hydroxide solution to pH=9 to 10, then shaken. The organic layer was dried, filtered, then concentrated under reduced pressure to give a residue, which was then purified by silica gel column chromatography (methylene chloride:methanol=20:1) to give the above-referenced compound, 4-(4-phenoxyphenyl)piperidine in an amount of 2.32 g (yield 66%).

Reference Example 8

Synthesis of 4-[4-(4-fluorophenyl)methylphenyl]piperidine

To a 25 ml ether solution of 2.5 g of 4-bromo-4'-fluorodiphenylmethane was gradually dropwise added at −78° C. a 6.5 ml of n-butyllithium (1.6 mol/l hexane solution). After being warmed up to −20° C., then stirred for 1 hour, an 8 ml tetrahydrofuran solution of 1.8 g of N-tert-butoxycarbonyl-4-piperidone was dropwise added. The mixture was stirred at 0° C. for 1 hour, then a 15 ml of saturated aqueous ammonium chloride solution was added and the product was extracted with ether. The extract was washed with saturated saline, dried, filtered, then concentrated under reduced pressure to give a residue, which was purified by silica gel column chromatography (hexane:ethyl acetate=4:1) to give N-tert-butoxycarbonyl-4-[4-(4-fluorophenyl)methylphenyl]-4-piperidinol in an amount of 2.69 g (yield 77%).

The obtained N-tert-butoxycarbonyl-4-[4-(4-fluorophenyl)methylphenyl]-4-piperidinol was used in the same way as Step B in Reference Example 7 to produce 4-[4-(4-fluorophenyl)methylphenyl]-1,2,3,6-tetrahydropyridine.

The obtained 4-[4-(4-fluorophenyl)methylphenyl]-1,2,3,6-tetrahydropyridine was used in the same way as Step C in Reference Example 7 to produce the above-referenced compound, 4-[4-(4-fluorophenyl)methylphenyl]piperidine.

Reference Example 9

Synthesis of 1-[4-(4-fluorophenyl)methylphenyl]piperazine

To a 10 ml acetonitrile solution of 426 mg of 4,4'-difluorobenzophenone and 841 mg of piperazine, 395 mg of triethylamine was added and stirred at 100° C. for 12 hours. After cooling to room temperature, saturated aqueous sodium hydrogenbicarbonate solution was added, followed by extracting with chloroform. The extract was dried, filtered and concentrated under reduced pressure. The residue obtained was dissolved in 5 ml of trifluoroacetic acid and treated with 520 mg of triethylsilane and 60 mg of concentrated sulfuric acid, and stirred at room temperature for 1 hour. The reaction mixture was adjusted to pH=9 to 11 with 10% aqueous sodium hydroxide solution, followed by extracting with ethyl acetate. The extract was dried, filtered and concentrated under reduced pressure to give a residue, which was purified by silica gel column chromatography (chloroform:methanol:water (2% acetic acid)=65:35:5) to give the above-referenced compound, 1-[4-(4-fluorophenyl)methylphenyl]piperazine in an amount of 305 mg (yield 58%).

Example 1

Synthesis of 4-[(4-fluorophenoxy)phenyl]piperidine (6)

To an 100 ml methanol solution of 1.25 g of the compound (4) synthesized in Reference Example 4 was added 200 mg of palladium carbon and 1 ml of acetic acid. The resultant mixture was hydrogenated under atmospheric pressure at room temperature. After the end of the reaction, the insolubles were filtered off, and the filtrate was concentratedunder reduced pressure. The residue thus obtained was then purified by silica gel column chromatography (methylene chloride:methanol=10:1) to give the above-referenced compound (6) in an amount of 1.17 g (yield 93%.).

Example 2

Synthesis of 4-(3-fluoro-4-phenyl)phenyl-4-piperidinol (8)

To a 50 ml methanol solution of 1.39 g of the compound (2) synthesized in Reference Example 2 was added 280 mg of palladium hydroxide. The resultant mixture was hydrogenated at room temperature under 5 atmospheres. After the end of the reaction, the insolubles were filtered off, the filtrate was concentrated under reduced pressure. The residue obtained was then purified by silica gel column chromatography (methylene chloride:methanol=10:1) to give the above-referenced compound (8) in an amount of 710 mg (yield 68%).

Example 3

Synthesis of (2S)-1-[4-(tert-butoxycarbonylamino)phenoxy]-2,3-epoxypropane (9)

To an 8 ml dimethylformamide suspension of 60 mg of sodium hydride was added, under ice cooling, 300 mg of 4-(tert-butoxycarbonylamino)phenol. The resultant mixture was stirred at room temperature for 1 hour. Under ice cooling, 372 mg of (S)-glycidyl 3-nitrobenzenesulfonate was gradually added, then the resultant mixture was stirred at room temperature for 2 hours. The reaction was quenched with a 5 ml of saturated aqueous ammonium chloride solution, then the product was extracted with ether. The extract was washed with saturated saline, dried, filtered, then concentrated under reduced pressure to give a residue, which was then purified by silica gel column.chromatography (hexane:ethyl acetate=3:1) to give the above-referenced compound (9) in an amount of 315 mg (yield 83%).

Example 4

Synthesis of (2S)-1-[(4-tert-butoxycarbonylamino-2 3 5-trimethyl)phenoxy]-2,3-epoxypropane (10)

The same procedure was followed as in Example 3 using (4-tert-butoxycarbonylamino-2,3,5-trimethyl)phenol to produce the above.

Example 5

Synthesis of (2S)-1-[(4-tert-butoxycarbonylamino-2,5-dimethyl)phenoxy]-2.3-epoxypropane (11)

The same procedure was followed as in Example 3 using (4-tert-butoxycarbonylamino-2,5-dimethyl)phenol to produce the above.

Example 6

Synthesis of (2S)-1-[(4-tert-butoxycarbonylamino-2,3-dimethyl)phenoxy]-2,3-epoxypropane (12)

The same procedure was followed as in Example 3 using (4-tert-butoxycarbonylamino-2,3-dimiethyl)phenol to produce the above.

Example 7

Synthesis of (2S)-1-[(4-tert-butoxycarbonylamino-2,3,6-trimethyl)phenoxy]-2,3-epoxypropane (13)

The same procedure was followed as in Example 3 using (4-tert-butoxycarbonylamino-2,3,6-trimethyl)phenol to produce the above.

Example 8

Synthesis of (2S)-1-[(5-tert-butoxycarbonylamino-2-methoxy)phenoxy]-2,3-epoxypropane (14)

The same procedure was followed as in Example 3 using (5-tert-butoxycarbonylamino-2-methoxy)phenol to produce the above.

Example 9

Synthesis of (2S)1-[(2-tert-butoxycarbonylamino-4,6-dimethyl)phenoxy]-2,3-epoxypropane (15)

The same procedure was followed as in Example 3 using (2-tert-butoxycarbonylamino-4,6-dimethyl)phenol to produce the above.

Example 10

Synthesis of (2S)-1-[(5-tert-butoxycarbonylamino-4-chloro-2-methoxy)phenoxy]-2,3-epoxypronane (16)

The same procedure was followed as in Example 3 using (5-tert-butoxycarbonylamino-4-chloro-2-methoxy)phenol to produce the above.

Example 11

Synthesis of (2S)-1-[(4-tert-butoxycarbonylamino-2,6-dichloro)phenoxy]-2,3-epoxypropane (17)

The same procedure was followed as in Example 3 using (4-tert-butoxycarbonylamino-2,6-chloro)phenol to produce the above.

Example 12

Synthesis of (2S)-1-[(4-tert-butoxycarbonylamino-2-chloro-3,5,6-trimethyl)phenoxy]-2,3-epoxyropane (18)

The same procedure was followed as in Example 3 using (4-tert-butoxycarbonylamino-2-chloro-3,5,6-trimethyl)phenol to produce the above.

Example 13

Synthesis of (2R)-1-[(4-tert-butoxycarbonylamino-2,3,5-trimethyl)phenoxy]-2,3-epoxypropane (19)

The same procedure was followed as in Example 3 using (4-tert-butoxycarbonylamino-2,3,5-trimethyl)phenol and (R)-glycidyl 3-nitrobenzenesulfonate to produce the above.

Example 14

Synthesis of (2R)-1-[(5-tert-butoxycarbonylamino-2-methoxy)phenoxy]-2,3-epoxopropane (20)

The same procedure was followed as in Example 3 using (5-tert-butoxycarbonylamino-2-methoxy)phenol and (R)-glycidyl 3-nitrobenzenesulfonate to produce the above.

Example 15

Synthesis of 1-chloro-3-[(4-methoxy-2-methyl)phenyl]amino-2-propanol (21)

A mixture of 300 mg of 4-methoxy-2-methylaniline and 213 mg of epichlorohydrin in 5 ml of isopropyl alcohol was stirred at 80° C. overnight. The reaction was concentrated under reduced pressure to give a residue, which was purified by silica gel column chromatography (methylene chloride:hexane:ethyl acetate=10:2:1) to give the above-referenced compound (21) in an amount of 315 mg (yield 63%).

Example 16

Synthesis of (2R)-1-chloro-3-[(4-methoxy-2-methyl)phenyl]amino-2-propanol (22)

The same procedure was followed as in Example 15 using (R)-epichlorohydrin to produce the above.

Example 17

Synthesis of (2S)-1-chloro-3-[(4-methoxy-2-methyl)phenyl]amino-2-propanol (23)

The same procedure was followed as in Example 15 using (S)-epichlorohydrin to produce the above.

Example 18

Synthesis of 1-chloro-3-[(4-tert-butoxycarbonylamino-2,3,5,6-tetramethyl)phenyl]amino-2-propanol (24)

The same procedure was followed as in Example 15 using (4-tert-butoxycarbonylamino-2,3,5,6-tetramethyl)aniline and epichlorohydrin to produce the above.

Example 19

Synthesis of (2S)-1-(4-aminophenoxy)-3-[4-(4-phenoxyphenyl)piperidin-1-yl]-2-propanol (25)

A mixture of 300 mg of the compound (9) synthesized in Example 3 and 287 mg of 4-(4-phenoxyphenyl)piperidine synthesized in Reference Example 7 in 8 ml of isopropyl alcohol was stirred at 100° C. for 2 hours. The reaction was concentrated under reduced pressure to give a residue. Under ice cooling, 5 ml of ethanol saturated with hydrochloric acid and 2 ml of trifluoroacetic acid were added. The resultant mixture was stirred at room temperature for 1 hour, then the solvent was removed under reduced pressure to give crude crystals, which were recrystallized to give the hydrochloric acid salts of the above-referenced compound (25) in an amount of 156 mg (yield 82%).

Example 20

Synthesis of (2S)-1-[(4-amino-2,3,5-trimethyl)phenoxy]-3-[4-(4-phenoxyphenyl)piperidin-1-yl]-2-propanol (26)

The compound (10) synthesized in Example 4 was used to produce the above in the same way as in Example 19.

Example 21

Synthesis of (2S)-1-[(4-amino-2,3,5-trimethyl)phenoxy]-3-[4-(4-(4-fluorophenyl)methylphenyl)piperidin-1-yl]-2-propanol (27)

The compound (10) synthesized in Example 4 and 4-[4-(4-fluorophenyl)methylphenyl]piperidine synthesized in Reference Example 8 were used to produce the above in the same way as in Example 19.

Example 22

Synthesis of (2S)-1-[(4-amino-2,3,5-trimethyl)phenoxy]-3-[4-(4-(4-fluorophenyl)methylphenyl)piperazin-1-yl]-2-propanol (28)

The compound (10) synthesized in Example 4 and 1-[4-(4-fluorophenyl)methylphenyl]piperazine synthesized in Reference Example 9 were used to produce the above in the same way as in Example 19.

Example 23

Synthesis of (2S)-1-[(4-amino-2,3,5-trimethyl)phenoxy]-3-[4-(4-(4-fluorophenoxy)phenyl)piperidin-1-yl]-2-propanol (29)

The compound (6) synthesized in Example 1 and the compound (10) synthesized in Example 4 were used to produce the above in the same way as in Example 19.

Example 24

Synthesis of (2S)-1-[(4-amino-2,3,5-trimethyl)phenoxy]-3-[4-(3-fluoro-4-phenylphenyl)-4-hydroxypiperidin-1-yl]-2-propanol (30)

The compound (8) synthesized in Example 2 and the compound (10) synthesized in Example 4 were used to produce the above in the same way as in Example 19.

Example 25

Synthesis of (2S)-1-[(4-amino-2,3,5-trimethyl)phenoxy]-3-[4-(4-cyclopentyloxyphenyl)piperidin-1-yl]-2-propanol (31)

The compound (7) synthesized in Reference Example 6 and the compound (10) synthesized in Example 4 were used to produce the above in the same way as in Example 19.

Example 26

Synthesis of (2S)-1-[(4-amino-2,5-dimethyl)phenoxy]-3-[4-(4-phenoxyphenyl)piperidin-1-yl]-2-propanol (32)

The compound (11) synthesized in Example 5 was used to produce the above in the same way as in Example 19.

Example 27

Synthesis of (2S)-1-[(4-amino-2,5-dimethyl)phenoxy]-3-[4-(4-(4-fluorophenyl)methylphenyl)piperidin-1-yl]-2-propanol (33)

The compound (11) synthesized in Example 5 and 4-[4-(4-fluorophenyl)methylphenyl]piperidine synthesized in Reference Example 8 were used to produce the above in the same way as in Example 19.

Example 28

Synthesis of (2S)-1-[g(4-amino-2,5-dimethyl)phenoxy]-3-[4-(4-(4-fluorophenyl)methylphenyl)piperazin-1-yl]-2-propanol (34)

The compound (11) synthesized in Example 5 and 1-[4-(4-fluorophenyl)methylphenyl]piperazine synthesized in Reference Example 9 were used to produce the above in the same way as in Example 19.

Example 29

Synthesis of (2S)-1-[(4-amino-2,3-dimethyl)phenoxy]-3-[4-(4-phenoxyphenyl)piperidin-1-yl]-2-propanol (35)

The compound (12) synthesized in Example 6 was used to produce the above in the same way as in Example 19.

Example 30

Synthesis of (2S)-1-[(4-amino-2,3-dimethyl)phenoxy]-3-[4-(4-(4-fluorophenyl)methylphenyl)piperidin-1-yl]-2-propanol (36)

The compound (12) synthesized in Example 6 and 4-[4-(4-fluorophenyl)methylphenyl]piperidine synthesized in Reference Example 8 were used to produce the above in the same way as in Example 19.

Example 31

Synthesis of (2S)-1-[(4-amino-2,3-dimethyl)phenoxy]-3-[4-(4-(4-fluorophenyl)methylphenyl)piperazin-1-yl]-2-propanol (37)

The compound (12) synthesized in Example 6 and 1-[4-(4-fluorophenyl)methylphenyl]piperazine synthesized in Reference Example 9 were used to produce the above in the same way as in Example 19.

Example 32

Synthesis of (2S)-1-[(4-amino-2,3,6-trimethyl)phenoxy]-3-[4-(4-phenoxyphenyl)piperidin-1-yl]-2-propanol (38)

The compound (13) synthesized in Example 7 was used to produce the above in the same way as in Example 19.

Example 33

Synthesis of (2S)-1-[(4-amino-2,3,6-trimethyl)phenoxy]-3-[4-(4-(4-fluorophenoxy)phenyl)piperidin-1-yl]-2-propanol (39)

The compound (6) synthesized in Example 1 and compound (13) synthesized in Example 7 were used to produce the above in the same way as in Example 19.

Example 34

Synthesis of (2S)-1-[(4-amino-2,3,6-trimethyl)phenoxy]-3-[4-(4-(4-fluorophenyl)methylphenyl)piperazin-1-yl]-2-propanol (40)

The compound (13) synthesized in Example 7 and the 1-[4-(4-fluorophenyl)methylphenyl]piperazine synthesized in Reference Example 9 were used to produce the above in the same way as in Example 19.

Example 35

Synthesis of (2S)-1-[(5-amino-2-methoxy)phenoxy]-3-[4-(4-phenoxyphenyl)piperidin-1-yl]-2-propanol (41)

The compound (14) synthesized in Example 8 was used to produce the above in the same way as in Example 19.

Example 36

Synthesis of (2S)-1-[(5-amino-2-methoxy)phenoxy]-3-[4-(4-(4-fluorophenoxy)phenyl)piperidin-1-yl]-2-propanol (42)

The compound (6) synthesized in Example 1 and the compound (14) synthesized in Example 8 were used to produce the above in the same way as in Example 19.

Example 37

Synthesis of (2S)-1-[(5-amino-2-methoxy)phenoxy]-3-[4-(4-(4-fluorophenyl)methylphenyl)piperidin-1-yl]-2-propanol (43)

The compound (14) synthesized in Example 8 and 4-[4-(4-fluorophenyl)methylphenyl]piperidine synthesized in Refer-

Example 38

Synthesis of (2S)-1-[(5-amino-2-methoxy)phenoxy]-3-[4-(4-(4-fluorophenyl)methylphenyl)piperazin-1-yl]-2-propanol (44)

The compound (14) synthesized in Example 8 and 1-[4-(4-fluorophenyl)methylphenyl]piperazine synthesized in Reference Example 9 were used to produce the above in the same way as in Example 19.

Example 39

Synthesis of (2S)-1-[(5-amino-2-methoxy)phenoxy]-3-[4-(4-cyclopentyloxyphenyl)piperazin-1-yl]-2-propanol (45)

The compound (7) synthesized in Reference Example 6 and the compound (14) synthesized in Example 8 were used to produce the above in the same way as in Example 19.

Example 40

Synthesis of (2S)-1-[(2-amino-4,6-dimethyl)phenoxy]-3-[4-(4-phenoxyphenyl)piperidin-1-yl]-2-propanol (46)

The compound (15) synthesized in Example 9 was used to produce the above in the same way as in Example 19.

Example 41

Synthesis of (2S)-1-[(2-amino-4,6-dimethyl)phenoxy]-3-[4-(4-(4-fluorophenyl)methylphenyl)piperidin-1-yl]-2-proyanol (47)

The compound (15) synthesized in Example 9 and 4-[4-(4-fluorophenyl)methylphenyl]piperidine synthesized in Reference Example 8 were used to produce the above in the same way as in Example 19.

Example 42

Synthesis of (2S)-1-[(2-amino-4,6-dimethyl)phenoxy]-3-[4-(4-(4-fluorophenyl)methylphenyl)piperazin-1-yl]-2-propanol (48)

The compound (15) synthesized in Example 9 and 1-[4-(4-fluorophenyl)methylphenyl]piperazine synthesized in Reference Example 9 were used to produce the above in the same way as in Example 19.

Example 43

Synthesis of (2S)-1-[(5-amino-4-chloro-2-methoxy)phenoxy]-3-[4-(4-phenoxyphenyl)piperidin-1-yl]-2-propanol (49)

The compound (16) synthesized in Example 10 was used to produce the above in the same way as in Example 19.

Example 44

Synthesis of (2S)-1-[(5-amino-4-chloro-2-methoxy)phenoxy]-3-[4-(4-(4-fluorophenyl)methylphenyl)pinerazin-1-yl]-2-propanol (50)

The compound (16) synthesized in Example 10 and 1-[4-(4-fluorophenyl)methylphenyl]piperazine synthesized in Reference Example 9 were used to produce the above in the same way as in Example 19.

Example 45

Synthesis of (2S)-1-[(4-amino-2,6-dichloro)phenoxy]-3-[4-(4-phenoxyphenyl)piperidin-1-yl]-2-propanol (51)

The compound (17) synthesized in Example 11 was used to produce the above in the same way as in Example 19.

Example 46

Synthesis of (2S)-1-[(4-amino-2,6-dichloro)phenoxy]-3-[4-(4-(4-fluorophenyl)methylphenyl)piperazin-1-yl]-2-propanol (52)

The compound (17) synthesized in Example 11 and 1-[4-(4-fluorophenyl)methylphenyl]piperazine synthesized in Reference Example 9 were used to produce the above in the same way as in Example 19.

Example 47

Synthesis of 1-[4-(4-phenoxyphenyl)piperidin-1-yl]-3-[(4-methoxy-2-methyl)phenylamino]-2-propanol (53)

A mixture of 91 g of the compound (21) synthesized in Example 15, 100 mg of the 4-(4-phenoxyphenyl)piperidine synthesized in Reference Example 7, and 109 mg of potassium carbonate in 4 ml of isopropyl alcohol was stirred at 80° C. for 3 hours. The insolubles 35 were filtered off, then the filtrate was concentrated under reduced pressure to give a residue. This was then purified by silica gel column chromatography (methylene chloride:methanol=30:1) to give the above-referenced compound (53) in an amount of 146 mg (yield 84%).

Example 48

Synthesis of 1-[4-(4-(4-fluorophenyl)methylphenyl)piperidin-1-yl]-3-[(4-methoxy-2-methyl)phenylamino]-2-propanol (54)

The same procedure was followed as in Example 47 using 4-[4-(4-fluorophenyl)methylphenyl]piperidine synthesized in Reference Example 8 to produce the above.

Example 49

Synthesis of 1-[4-(4-(4-fluorophenyl)methylphenyl)piperazin-1-yl]-3-[(4-methoxy-2-methyl)phenylamino]-2-propanol (55)

The same procedure was followed as in Example 47 using 1-[4-(4-fluorophenyl)methylphenyl]piperazine synthesized in Reference Example 9 to produce the above.

Example 50

Synthesis of (2R)-1-[4-(4-phenoxyphenyl)piperidin-1-yl]-3-[(4-methoxy-2-methyl)phenylamino]-2-propanol (56)

The compound (22) synthesized in Example 16 was used to produce the above in the same way as in Example 47.

Example 51

Synthesis of (2S)-1-[4-(4-phenoxyphenyl)piperidin-1-yl]-3-[(4-methoxy-2-methyl)phenylamino]-2-propanol (57)

The compound (23) synthesized in Example 17 was used to produce the above in the same way as in Example 47.

Example 52

Synthesis of 3-[(4-amino-2,3,5,6-tetramethyl)phenylamino]-1-[4-(4-phenoxyphenyl)piperidin-1-yl]-2-propanol (58)

The compound (24) synthesized in Example 18 was used to produce the above in the same way as in Example 19.

Example 53

Synthesis of (2S)-1-[(4-amino-2-chloro-3,5,6-trimethyl)phenoxy]-3-[4-(4-phenoxyphenyl)piperidin-1-yl]-2-propanol (59)

The compound (18) synthesized in Example 12 was used to produce the above in the same way as in Example 19.

Example 54

Synthesis of (2R)-1-[(4-amino-2,3,5-trimethyl)phenoxy]-3-[4-(4-(4-fluorophenyl)methylphenyl)piperazin-1-yl]-2-propanol (60)

The compound (19) synthesized in Example 13 and 1-[4-(4-fluorophenyl)methylphenyl]piperazine synthesized in Reference Example 9 were used to produce the above in the same way as in Example 19.

Example 55

Synthesis of (2R)-1-[(5-amino-2-methoxy)phenoxy]-3-[4-(4-phenoxyphenyl)piperidin-1-yl]-2-propanol (61)

The compound (20) synthesized in Example 14 was used to produce the above in the same way as in Example 19.

Example 56

Synthesis of (2S)-1-[(4-amino-2,3,5-trimethyl)phenoxy]-3-[4-(4-(4-fluorophenyl)methylphenyl)piperazin-1-yl]-2-propanol dimethanesulfonate (62)

A 10 ml isopropyl alcohol solution of 480 mg of the compound (10) synthesized in Example 3 and 432 mg of 1-[4-(4-fluorophenyl)methylphenyl]piperazine was stirred at 100° C. for 2 hours. To the reaction mixture, 0.65 ml of concentrated hydrochloric acid was added and, after heating at reflux for 1 hour, the mixture was adjusted to pH=8 to 10 with 10% aqueous sodium hydroxide solution and the corresponding free base was extracted therefrom with ethyl acetate. The solvent was removed under reduced pressure to give the residue, which was then treated with 306 mg (i.e., 2 equivalents) of methanesulfonic acid in a conventional manner. The resultant crude crystal was purified by recrystallization to give the above-referenced compound (62) in an amount of 940 mg (yield 88%).

Example 57

Synthesis of (2S)-1-[(5-amino-2-methoxy)phenoxy]-3-[4-(4-phenoxyphenyl)piperidin-1-yl]-2-propanol p-toluenesulfonate (63)

The same procedure was followed as in Example 56 using the compound (14) synthesized in Example 8 and 4-(4-phenoxyphenyl)piperidine synthesized in Reference Example 7 to give the corresponding free base, followed by treating with an equivalent of p-toluenesulfonic acid to produce the above-referenced compound.

Example 58

Synthesis of (2S)-1-[(4-amino-2,3,5-trimethyl)phenoxy]-3-[4-(4-(4-fluorophenyl)methylphenyl)piperazin-1-yl]-2-propanol dihydrochloride (64)

The same procedure was followed as in Example 56 to give the corresponding free base, followed by treating with 2 equivalents of hydrochloric acid to produce the above referenced compound.

Example 59

Synthesis of (2S)-1-[(4-Amino-2,3,5-trimethyl)phenoxy]-3-[4-(4-(4-fluorophenyl)methylphenyl)piperazin-1-yl]-2-propanol ½sulfonate (65)

The above compound was synthesized by treating the corresponding free base with ½ equivalent of sulfuric acid in the same way as in Example 56.

Example 60

Synthesis of (2S)-1-[(4-Amino-2,3,5-trimethyl)phenoxy]-3-[4-(4-(4-fluorophenyl)methylphenyl)piperazin-1-yl]-2-propanol sulfonate (66)

The above compound was synthesized by treating the corresponding free base with an equivalent of sulfuric acid in the same way as in Example 56.

The physical data of the compounds obtained in the Reference Examples and Examples are shown in Table 1.

TABLE 1

| Compound no. | Chemical structure | Properties | IR (CHCl₃) | ¹H-NMR (CDCl₃) |
|---|---|---|---|---|
| 1 | 4-fluorophenoxy-phenyl-(N-Boc-4-hydroxypiperidine) | Colorless oily substance | 3020, 2402, 1676, 1499, 1430, 1368, 1249, 1168, 1089, 1029, 931, 832 | 1.41(s,9H), 1.68(2H, m), 1.97(2H, m), 3.19(2H, m), 3.95(2H, m), 6.85-7.05(4H, m), 6.87(2H,d), 7.35(2H, d) |
| 2 | 2-fluoro-biphenyl-(N-benzyl-4-hydroxypiperidine) | Colorless oily substance | 2946, 2817, 1706, 1483, 1406, 1367, 1345, 1119 | 1.76(2H, m), 2.18(2H, m), 2.48(2H, m), 2.79-2.83(2H, m), 3.60(2H, s), 7.29-7.45(11H, m), 7.54(2H, d) |
| 3 | cyclopentyloxy-phenyl-(N-Boc-4-hydroxypiperidine) | Pale yellow oily substance | 3011, 2971, 1682, 1609, 1509, 1478, 1430, 1367, 1279, 1269, 1086, 1030, 986 | 1.48(s, 9H), 1.58-1.66(2H, m), 1.72-1.99(10H, m), 3.25(2H, m), 3.97(2H, m), 4.75(1H, m), 6.85(2H, d), 7.35(2H, d) |
| 4 | 4-fluorophenoxy-phenyl-(1,2,3,6-tetrahydropyridine) | Colorless crystal | 2926, 1498, 1249, 1206, 1194, 1100, 1012, 816 | 2.37(2H, m), 3.04(2H, t), 3.46(2H, m), 6.01(1H, m), 6.84(2H, d), 6.86-6.98(4H, m), 7.26(2H, d) |
| 5 | cyclopentyloxy-phenyl-(1,2,3,6-tetrahydropyridine) | Yellow crystal | 2963, 1606, 1509, 1438, 1358, 1317, 1274, 1177, 1114, 1090, 988 | 1.56-1.66(2H, m), 1.75-1.94(6H, m), 2.40-2.44(2H, m), 3.09(2H, t), 3.51(2H, m), 4.74(1H, m), 6.02(1H, m), 6.82(2H, d), 7.29(2H, d) |

TABLE 1-continued

| # | Structure | Appearance | IR | NMR |
|---|---|---|---|---|
| 6 | 4-fluorophenoxy-phenyl-piperidine | Colorless oily substance | 2937, 1606, 1498, 1450, 1318, 1252, 1168, 1091, 1013, 832 | 1.56(2H, td), 1.77(2H, m), 2.53(H, t), 2.68(2H, td), 3.12(2H, m), 6.83(2H, m), 6.86-6.97(4H, m), 7.10(2H, d) |
| 7 | cyclopentyloxy-phenyl-piperidine | Pale yellow crystal | 2940, 1610, 1509, 1445, 1364, 1318, 1177, 1136, 1101, 1051, 989 | 1.55-1.64(4H, m), 1.77-1.89(8H, m), 2.54(1H, m), 2.72(2H, d), 3.17(2H, m), 4.72(1H, m), 6.81(2H, d), 7.10(2H, d) |
| 8 | 2-fluorobiphenyl-piperidinol | Colorless crystal | 3589, 2950, 1484, 1406, 1320, 1270, 1134, 1010 | 1.75-1.78(2H, m), 2.01-2.08(2H, m), 2.99-3.02(2H, m), 3.10-3.16(2H, m), 7.31-7.38(3H, m), 7.42-7.46(3H, m), 7.54-7.56(2H, m) |
| 9 | Boc-aminophenyl glycidyl ether | Colorless crystal $[\alpha]_D + 2°$ (c = 1.4, CHCl$_3$) | 3439, 3018, 2981, 1720, 1596, 1518, 1457, 1412, 1368, 1157, 1041, 918 | 1.44(9H, s), 2.67(1H, dd), 2.81(1H, dd), 3.26(1H, m), 3.87(1H, dd), 4.09(1H, dd), 6.24(1H, brs), 6.80(2H, d), 7.19(2H, d) |
| 10 | Boc-amino-dimethylphenyl glycidyl ether | Colorless crystal $[\alpha]_D + 3.1°$ (c = 1.1, CHCl$_3$) | 3431, 2980, 2400, 1718, 1491, 1368, 1322, 1163, 1121, 1049, 929, 845 | 1.54(9H, s), 2.18(3H, s), 2.20(3H, s), 2.25(3H, s), 2.78(1H, dd), 2.90(1H, dd), 3.37(1H, m), 3.98(1H, dd), 4.18(1H, dd), 5.79(1H, brs), 6.59(1H, d) |
| 11 | Boc-amino-trimethylphenyl glycidyl ether | Light brown crystal $[\alpha]_D + 2.52°$ (c = 1.19, CHCl$_3$) | 3019, 1720, 1522, 1485, 1456, 1409, 1393, 1368, 1313, 1159, 1116 | 1.50(9H, s), 2.20(6H, s), 2.75(1H, m), 2.88(1H, m), 3.33(1H, m), 3.94(1H, dd), 4.15(1H, dd), 6.01(1H, brs), 6.62(1H, s), 7.39(1H, s) |

TABLE 1-continued

| | Structure | Appearance | IR | NMR |
|---|---|---|---|---|
| 12 | (2,3-dimethyl-4-BocNH-phenyl, glycidyl ether) | Light brown crystal [α]$_D$ +5.14° (c = 1.05, CHCl$_3$) | 3019, 1719, 1603, 1491, 1458, 1420, 1393, 1368, 1159, 1090 | 1.50(9H, s), 2.16(3H, s), 2.19(3H, s), 2.75(1H, dd), 2.88(1H, dd), 3.32-3.36(1H, m), 3.94(1H, dd), 4.18(1H, dd), 6.05(1H, brs), 6.69(1H, d), 7.27(1H, d) |
| 13 | (2,3,5-trimethyl-4-BocNH-phenyl, glycidyl ether) | Colorless foamy substance [α]$_D$ +0.98° (c = 0.82, CHCl$_3$) | 3436, 2981, 2401, 1719, 1603, 1452, 1508, 1393, 1368, 1159, 1091, 1008, 914, 837 | 1.53(9H, s), 2.14(3H, s), 2.24(3H, s), 2.29(3H, s), 2.75(1H, dd), 2.89(1H, dd), 3.37(1H, m), 3.71(1H, dd), 3.96(1H, dd), 6.12(1H, brs), 7.28(1H, s) |
| 14 | (4-OMe-3-BocNH-phenyl, glycidyl ether) | Pale yellow crystal [α]$_D$ −3.24° (c = 1.05, CHCl$_3$) | 3018, 1720, 1603, 1518, 1464, 1442, 1426, 1406, 1394, 1368, 1318, 1292, 1159, 1027 | 1.51(9H, s), 2.75(1H, dd), 2.88(1H, dd), 3.38(1H, m), 3.83(3H, s), 4.05(1H, dd), 4.24(1H, dd), 6.32(1H, dd), 6.79(2H, s), 7.17(1H, s) |
| 15 | (3,5-dimethyl-2-NHBoc-phenyl, glycidyl ether) | Brown oily substance [α]$_D$ +13.7° (c = 1.21, CHCl$_3$) | 3020, 1719, 1609, 1522, 1448, 1393, 1368, 1285, 1159, 1105, 1008 | 1.53(9H, s), 2.24(3H, s), 2.26(3H, s), 2.86(1H, dd), 2.91(1H, s), 3.31(1H, m), 3.89(1H, dd), 4.01(1H, dd), 6.61(1H, s), 7.40(1H, brs), 7.75(1H, s) |
| 16 | (5-Cl-2-OMe-4-BocNH-phenyl, glycidyl ether) | Colorless crystal [α]$_D$ +0.88° (c = 0.9, CHCl$_3$) | 3425, 3019, 2982, 1721, 1594, 1522, 1485, 1464, 1442, 1410, 1369, 1326, 1237, 1075 | 1.56(9H, s), 2.80(1H, dd), 2.92(1H, dd), 3.42(1H, m), 3.84(3H, s), 4.09(1H, dd), 4.27(1H, dd), 6.80(1H, s), 6.87(1H, s), 7.84(1H, s) |
| 17 | (2,6-dichloro-4-BocNH-phenyl, glycidyl ether) | Colorless crystal [α]$_D$ −1.1° (c = 1.1, CHCl$_3$) | 3018, 1721, 1601, 1486, 1456, 1393, 1368, 1342, 1302, 1161, 1116, 1090, 1048 | 1.53(9H, s), 2.72(1H, dd), 2.89(1H, dd), 3.45(1H, m), 4.05(1H, dd), 4.16(1H, dd), 6.42(1H, brs), 7.39(2H, s) |

| | Structure | Appearance | IR | NMR |
|---|---|---|---|---|
| 18 | (2,6-dimethyl-3-chloro-4-BocNH phenoxymethyl epoxide) | Colorless crystal [α]_D −0.78° (c = 1.02, CHCl_3) | 3019, 1721, 1484, 1456, 1393, 1368, 1321, 1161, 1117, 1094, 1045, 1015 | 1.55(9H, s), 2.16(3H, s), 2.24(3H, s), 2.30(3H, s), 2.72(1H, dd), 2.88(1H, s), 3.40(1H, m), 3.82(1H, m), 4.10(1H, dd), 7.26(1H, brs) |
| 19 | (2,3,5-trimethyl-4-BocNH phenoxymethyl epoxide) | Colorless crystal [α]_D −3.1° (c = 1.03, CHCl_3) | 3431, 2980, 2400, 1718, 1603, 1518, 1491, 1368, 1322, 1163, 1121, 1049, 929, 845 | 1.54(9H, s), 2.18(3H, s), 2.20(3H, s), 2.25(3H, s), 2.78(1H, dd), 2.90(1H, dd), 3.37(1H, m), 3.98(1H, dd), 4.18(1H, dd), 5.79(1H, brs), 6.59(1H, d) |
| 20 | (3-BocNH-4-OMe phenoxymethyl epoxide) | Pale yellow crystal [α]_D +3.24° (c = 1.32, CHCl_3) | 3018, 1720, 1603, 1518, 1464, 1442, 1426, 1406, 1394, 1368, 1318, 1292, 1159, 1027 | 1.51(9H, s), 2.75(1H, dd), 2.88(1H, m), 3.38(1H, m), 3.83(3H, s), 4.05(1H, dd), 4.24(1H, dd), 6.32(1H, brs), 6.79(2H, s), 7.17(1H, s) |
| 21 | (1-chloro-3-(2-methyl-4-methoxyanilino)-2-propanol) | Light brown oily substance | 3019, 1509, 1466, 1444, 1420, 1380, 1289, 1162, 1082, 1050 | 2.17(3H, m), 2.48(1H, m), 3.22(1H, dd), 3.37(1H, dd), 3.63-3.73(2H, m), 3.74(3H, s), 4.09-4.10(1H, m), 6.60(1H, d), 6.68-6.71(2H, m) |
| 22 | ((S)-1-chloro-3-(2-methyl-4-methoxyanilino)-2-propanol) | Light brown crystal [α]_D +5.59° (c = 1.11, MeOH) | 3016, 1510, 1465, 1421, 1380, 1289, 1162, 1081, 1050 | 2.17(3H, m), 2.50(1H, m), 3.22(1H, dd), 3.37(1H, dd), 3.63-3.73(2H, m), 3.74(3H, s), 4.10(1H, m), 6.60(1H, d), 6.68-6.71(2H, m) |
| 23 | ((R)-1-chloro-3-(2-methyl-4-methoxyanilino)-2-propanol) | Brown crystal [α]_D −5.59° (c = 1.04, MeOH) | 3017, 1510, 1465, 1420, 1380, 1289, 1162, 1081, 1050 | 2.16(3H, m), 2.50(1H, m), 3.22(1H, dd), 3.37(1H, dd), 3.63-3.73(2H, m), 3.74(3H, s), 4.10(1H, m), 6.60(1H, d), 6.68-6.71(2H, m) |

TABLE 1-continued

| Compound no. | Chemical Structure | Properties Melting point (recrystallization solvent) | IR (KBr) | $^1$H-NMR (d$_6$-DMSO) | MS or elementary analysis |
|---|---|---|---|---|---|
| 24 | Structure: tetramethylphenyl with BocNH and NH-CH2-CH(OH)-CH2-Cl | Colorless crystal | 3431, 3019, 2981, 1719, 1485, 1392, 1368, 1163, 1047, 1021 | 1.56(3H, s), 2.23(6H, s), 2.28(6H, s), 2.78(1H, brs), 3.01(1H, dd), 3.05(1H, dd), 3.65-3.75(2H, m), 4.05(1H, m), 5.91(1H, brs) | |
| 25 | Structure: 4-(4-phenoxyphenyl)piperidine with N-CH2-CH(OH)-CH2-O-C6H4-NH2, 2HCl | Colorless crystal >235° C. (decomposition) (methanol/ether) [α]$_D$ −9.58° (c = 0.48, MeOH) | 3356, 2858, 2574, 1988, 1611, 1590, 1490, 1305, 1256, 1170, 1135, 1071, 981, 827 | 1.90-2.20(4H, m), 2.85(1H, m), 3.15-3.40(4H, m), 3.68(2H, m), 3.98(2H, m), 4.39(1H, m), 6.98(6H, m), 7.14(3H, m), 7.25(2H, d), 7.39(2H, m) | MS(FAB/free base) m/z: 419(M + H$^+$) |
| 26 | Structure: 4-(4-phenoxyphenyl)piperidine with N-CH2-CH(OH)-CH2-O-(2,6-dimethyl-4-aminophenyl), 2HCl | Colorless crystal >225° C. (decomposition) (2-propanol/ether) [α]$_D$ −26.8° (c = 0.4, MeOH) | 3142, 2932, 2604, 1676, 1590, 1420, 1327, 1234, 1130, 1023, 979, 870 | 1.95-2.18(4H, m), 2.14(3H, s), 2.23(3H, s), 2.32(3H, s), 2.84(1H, m), 3.15-3.35(4H, m), 3.68(2H, m), 3.97(2H, s), 4.43(1H, m), 6.79(1H, s), 6.99(4H, d), 7.14(1H, t), 7.27(2H, d), 7.39(2H, t) | $C_{29}H_{38}Cl_2N_2O_3 \cdot 2\ 3/4 H_2O$ (dihydrochloride)<br>C H N<br>Calcd: 59.74 6.57 4.80<br>Found: 59.76 6.79 4.78 |

TABLE 1-continued

| | Structure | Properties | IR | NMR | MS/Elemental Analysis |
|---|---|---|---|---|---|
| 27 | (4-fluorobenzyl-phenyl-piperidine with aminophenol ether propanol, 2HCl) | Colorless crystal 225-230° C. (methanol/ether) $[\alpha]_D$ −9.35° (c = 1.07, MeOH) | 2928, 1630, 1589, 1508, 1488, 1469, 1416, 1393, 1330, 1286, 1217, 1158, 1128, 1099 | 1.91-2.11(4H, m), 2.13(3H, s), 2.24(3H, s), 2.34(3H, s), 2.76-2.82(1H, m), 3.12-3.41(4H, m), 3.66(2H, m), 3.90(2H, s), 3.92-4.00(2H, m), 4.44(1H, m), 6.80(1H, s), 7.09(2H, m), 7.18(4H, m), 7.23-7.27(2H, m) | MS (FAB/free base) m/z: 477(M + H$^+$) |
| 28 | (4-fluorobenzyl-phenyl-piperazine with aminophenol ether propanol, 3HCl) | Colorless crystal 197-198° C. (methanol/ether) $[\alpha]_D$ −8.36° (c = 0.67, MeOH) | 3384, 2928, 1627, 1600, 1508, 1460, 1327, 1287, 1219, 1127, 1017, 982, 824, 769 | 2.14(3H, s), 2.27(3H, s), 2.37(3H, s), 3.15-3.80(10H, m), 3.97(2H, m), 4.46(1H, m), 6.83(1H, s), 6.94(2H, d), 7.10(4H, m), 7.23(2H, dd) | $C_{29}H_{38}Cl_3FN_4O_2 \cdot 1/2H_2O$ (trihydrochloride)<br>  C      H      N<br>Calcd: 58.44  6.60  7.05<br>Found: 58.36  6.50  7.02 |
| 29 | (4-fluorophenoxy-phenyl-piperidine with aminophenol ether propanol, 2HCl) | Colorless crystal 260-263° C. (2-propanol/ether) $[\alpha]_D$ −8.08° (c = 1.04, MeOH) | 2928, 1590, 1499, 1418, 1327, 1287, 1249, 1214, 1193, 1171, 1127, 1092 | 1.98-2.09(4H, m), 2.14(3H, s), 2.24(3H, s), 2.35(3H, s), 2.83(1H, m), 3.19-3.34(4H, m), 3.67(2H, m), 3.94-3.99(2H, m), 4.44(1H, m), 6.80(1H, s), 6.97(2H, d), 7.03-7.06(2H, m), 7.19-7.27(4H, m) | $C_{29}H_{37}Cl_2FN_2O_3 \cdot 3/4H_2O$ (dihydrochloride)<br>  C      H      N<br>Calcd: 61.65  6.60  4.96<br>Found: 61.70  6.79  4.77 |

| | Structure | Properties | IR (cm⁻¹) | ¹H NMR | Formula / Analysis |
|---|---|---|---|---|---|
| 30 | [structure: 4-amino-2,3,5-trimethylphenoxy-CH2-CH(OH)-CH2-N-piperidine-4(OH)-(2-fluoro-biphenyl)], 2HCl | Colorless crystal 242–244° C. (methanol/ether) [α]_D −8.47° (c = 1.11, MeOH) | 2936, 2871, 1626, 1590, 1518, 1485, 1467, 1407, 1327, 1284, 1268, 1235, 1215, 1133 | 1.87(2H, m), 2.15(3H, s), 2.25(3H, s), 2.35(3H, s), 2.46-2.55(2H, m), 3.24-3.45(4H, m), 3.57(2H, m), 3.97(2H, s), 4.47(1H, m), 6.80(1H, s), 7.37-7.42(3H, m), 7.48(2H, m), 7.54(3H, m) | C₂₉H₃₇Cl₃FN₂O₃·1/4H₂O (dihydrochloride)<br>C H N<br>Calcd: 62.65 6.71 5.04<br>Found: 62.73 6.70 5.04 |
| 31 | [structure: 4-amino-2,3,5-trimethylphenoxy-CH2-CH(OH)-CH2-N-piperidine-4-(4-cyclopentyloxyphenyl)], 2HCl | Colorless crystal 225–228° C. (2-propanol/ether) [α]_D −9.74° (c = 1.17, MeOH) | 2957, 2870, 1612, 1590, 1512, 1489, 1460, 1418, 1327, 1286, 1244, 1180, 1128, 979 | 1.57-1.70(6H, m), 1.87-2.09(6H, m), 2.14(3H, s), 2.24(3H, s), 2.34(3H, s), 2.75(1H, m), 3.12-3.34(4H, m), 3.66(2H, m), 3.91-4.00(2H, m), 4.44(1H, m), 4.76(1H, m), 6.79(1H, m), 6.85(2H, d), 7.13(2H, d) | C₂₈H₄₂Cl₃N₂O₃·1.1/4H₂O (dihydrochloride)<br>C H N<br>Calcd: 61.36 7.72 5.11<br>Found: 61.34 7.82 5.14 |
| 32 | [structure: 4-amino-2,3,5-trimethylphenoxy-CH2-CH(OH)-CH2-N-piperidine-4-(4-phenoxyphenyl)], 2HCl | Colorless crystal 239–242° C. (methanol/ether) [α]_D −9.67° (c = 1.22, MeOH) | 2928, 2602, 1634, 1590, 1510, 1490, 1468, 1409, 1286, 1240, 1209, 1171, 1103 | 2.00-2.13(4H, m), 2.17(3H, s), 2.28(3H, s), 2.84(1H, m), 3.16-3.30(4H, m), 3.66-3.67(2H, m), 3.94-4.03(2H, m), 4.41(1H, m), 6.91(1H, s), 6.99(4H, d), 7.13(2H, m), 7.27(2H, d), 7.38(2H, t) | C₂₈H₃₆Cl₂N₂O₃·1/4H₂O (dihydrochloride)<br>C H N<br>Calcd: 64.18 6.92 5.35<br>Found: 64.02 6.98 5.42 |

TABLE 1-continued

| # | Structure | | | Analysis |
|---|---|---|---|---|
| 33 | [4-fluorobenzyl-phenyl-piperidine with HO-CH-CH2-O-dimethylaminophenyl] 2HCl | Colorless crystal 209–212° C. (ethanol/ether) [α]_D −11.9° (c = 1.08, MeOH) | 2926, 2596, 1633, 1602, 1508, 1460, 1412, 1286, 1209, 1158, 1102 | 1.91-2.09(4H, m), 2.15(3H, s), 2.24(3H, s), 2.80(1H, m), 3.20-3.29(4H, m), 3.65(2H, m), 3.90(2H, s), 3.90-3.97(2H, m), 4.38(1H, m), 6.86(1H, s), 7.01-7.27(9H, m) | $C_{28}H_{37}Cl_2FN_2O_3$ (dihydrochloride)<br>C H N<br>Calcd: 65.04 6.94 5.23<br>Found: 64.76 6.89 5.20 |
| 34 | [4-fluorobenzyl-phenyl-piperazine with HO-CH-CH2-O-dimethylaminophenyl] 3HCl | Colorless crystal 213–215° C. (methanol/ether) [α]_D −7.86° (c = 1.17, MeOH) | 2600, 1603, 1514, 1460, 1408, 1285, 1209, 1158, 1103, 1022 | 2.17(3H, s), 2.33(3H, s), 3.14-3.31(5H, m), 3.38-3.41(1H, m), 3.60-3.77(4H, m), 3.84(2H, s), 3.95-4.04(2H, m), 4.47(1H, m), 6.93(3H, m), 7.06-7.12(4H, m), 7.22(3H, m) | $C_{26}H_{33}Cl_3FN_3O_2$ (trihydrochloride)<br>C H N<br>Calcd: 58.70 6.51 7.33<br>Found: 58.84 6.45 7.39 |
| 35 | [phenoxy-phenyl-piperidine with HO-CH-CH2-O-dimethylaminophenyl] 2HCl | Colorless crystal 242–245° C. (methanol/ether) [α]_D −9.49° (c = 1.37, MeOH) | 2928, 2599, 1590, 1508, 1490, 1312, 1272, 1242, 1212, 1170, 1112, 1073 | 1.99-2.13(4H, m), 2.18(3H, s), 2.22(3H, s), 2.84(1H, m), 3.15-3.32(4H, m), 3.68(2H, m), 3.96-4.01(2H, m), 4.46(1H, m), 6.91(1H, d), 6.99(4H, m), 7.13(1H, dd), 7.27(3H, m), 7.38(2H, m) | $C_{28}H_{36}N_2O_3Cl_2 \cdot 1/4H_2O$ (dihydrochloride)<br>C H N<br>Calcd: 64.18 6.92 5.35<br>Found: 64.05 6.87 5.34 |
| 36 | [4-fluorobenzyl-phenyl-piperidine with HO-CH-CH2-O-dimethylaminophenyl] 2HCl | Colorless crystal 237–240° C. (methanol/ether) [α]_D −21.0° (c = 1.05, MeOH) | 3294, 2605, 1601, 1508, 1486, 1460, 1432, 1315, 1274, 1220, 1213, 1159, 1138, 1113 | 1.91-2.14(4H, m), 2.18(3H, s), 2.22(3H, s), 2.79(1H, m), 3.10-3.32(4H, m), 3.66(2H, m), 3.90(2H, s), 3.93-4.01(2H, m), 4.45(1H, m), 6.90(1H, d), 7.09(2H, t), 7.18(4H, m), 7.23-7.27(3H, m) | $C_{29}H_{37}Cl_2FN_2O_2 \cdot 1.4H_2O$ (dihydrochloride)<br>C H N<br>Calcd: 64.50 6.91 5.19<br>Found: 64.64 6.93 5.19 |

TABLE 1-continued

| | Structure | Properties | IR | NMR | MS/Analysis |
|---|---|---|---|---|---|
| 37 | [structure: 2,3-dimethyl-4-amino-phenoxy-CH2-CH(OH)-CH2-piperazine-N-C6H4-CH2-C6H4-F], 3HCl | Colorless crystal 232-234° C. (methanol/ether) [α]_D −9.15° (c = 1.18, MeOH) | 3294, 2844, 2604, 1612, 1601, 1506, 1486, 1456, 1273, 1259, 1212, 1159, 1139, 1116, 977, 920 | 2.18(3H, s), 2.22(3H, s), 3.17-3.34(6H, m), 3.66-3.74(4H, m), 3.84(2H, s), 3.93-4.01(2H, m), 4.45(1H, m), 6.92(3H, m), 7.06-7.12(4H, m), 7.21-7.28(3H, m) | MS(FAB/free base) m/z:464(M + H⁺) |
| 38 | [structure: 2,3,5-trimethyl-4-amino-phenoxy-CH2-CH(OH)-CH2-piperidine-C6H4-O-C6H5], 2HCl | Colorless crystal 229-231° C. (methanol/ether) [α]_D −11.08° (c = 0.83, MeOH) | 3334, 2926, 2656, 1589, 1509, 1490, 1310, 1249, 1229, 1172, 1101, 871, 840 | 1.92-2.20(4H, m), 2.18(3H, s), 2.22(3H, s), 2.25(3H, s), 2.84(1H, m), 3.20(2H, m), 3.40(2H, m), 3.72(4H, m), 4.46(1H, m), 7.00(4H, d), 7.11(1H, s), 7.14(1H, t), 7.27(2H, d), 7.39(2H, t) | C₂₉H₃₆Cl₂N₂O₃ (dihydrochloride) C H N Calcd: 65.29 7.18 5.25 Found: 65.18 7.16 5.24 |
| 39 | [structure: 2,3,5-trimethyl-4-amino-phenoxy-CH2-CH(OH)-CH2-piperidine-C6H4-O-C6H4-F], 2HCl | Colorless crystal 258-260° C. (methanol/ether) [α]_D −10.4° (c = 1.10, MeOH) | 2928, 2886, 1587, 1498, 1456, 1310, 1216, 1193, 1171, 1137, 1094, 1058, 1013, 977 | 1.95-2.13(4H, m), 2.18(3H, s), 2.21(3H, s), 2.24(3H, s), 2.83(1H, m), 3.15-3.33(4H, m), 3.68-3.73(4H, m), 4.44(1H, m), 6.97(2H, d), 7.03-7.06(2H, m), 7.09(1H, s), 7.20-7.27(4H, m) | C₂₉H₃₇Cl₂FN₂O₃ (dihydrochloride) C H N Calcd: 63.16 6.76 5.08 Found: 63.48 6.68 4.97 |
| 40 | [structure: 2,3-dimethyl-4-amino-phenoxy-CH2-CH(OH)-CH2-piperazine-N-C6H4-CH2-C6H4-F], 3HCl | Colorless crystal 237-240° C. (methanol/ether) [α]_D −9.19° (c = 1.11, MeOH) | 2926, 2598, 1602, 1511, 1483, 1456, 1414, 1310, 1225, 1158, 1095, 1017, 984, 928 | 2.19(3H, s), 2.21(3H, s), 2.25(3H, s), 3.14-3.37(5H, m), 3.48(1H, m), 3.64-3.78(6H, m), 3.85(2H, s), 4.67(1H, m), 6.94(2H, d)d, 7.06-7.16(5H, m), 7.22(2H, m) | C₂₉H₃₈Cl₃FN₃O₂ (trihydrochloride) C H N Calcd: 59.34 6.70 7.16 Found: 59.50 6.65 7.15 |

TABLE 1-continued

| | Structure | Properties | IR | NMR | MS/Analysis |
|---|---|---|---|---|---|
| 41 | [structure: 4-phenoxyphenyl-piperidine linked via CH2-CH(OH)-CH2-O to 2-methoxy-5-aminophenyl; 2HCl] | Colorless crystal 90-92° C. (ether/methylene chloride) [α]$_D$ −8.24° (c = 1.19, MeOH) | 3384, 2936, 2599, 1590, 1520, 1471, 1447, 1349, 1236, 1167, 1021, 975, 870, 749 | 1.90-2.20(4H, m), 2.84(1H, m), 3.15-3.45(4H, m), 3.68(2H, m), 3.79(3H, s), 3.98(2H, m), 4.44(1H, m), 6.87(1H, d), 6.95-7.05(6H, m), 7.14(1H, t), 7.27(2H, d), 7.39(2H, t) | MS(FAB/free base) m/z:449(M + H$^+$) |
| 42 | [structure: 4-(4-fluorophenoxy)phenyl-piperidine linked via CH2-CH(OH)-CH2-O to 2-methoxy-5-aminophenyl; 2HCl] | Colorless crystal 155-156° C. (ether/methylene chloride) [α]$_D$ −8° (c = 1.1, MeOH) | 3410, 2942, 1672, 1609, 1504, 1349, 1216, 1091, 1023, 976, 876, 834, 752, 721 | 1.95-2.20(4H, m), 2.85(1H, m), 3.10-3.45(4H, m), 3.78(2H, m), 3.79(3H, s), 3.97(2H, m), 4.45(1H, m), 6.91(1H, d), 6.97(2H, d), 7.04(4H, m), 7.23(4H, m) | MS(FAB/free base) m/z: 467(M + H$^+$) |
| 43 | [structure: 4-(4-fluorobenzyl)phenyl-piperidine linked via CH2-CH(OH)-CH2-O to 2-methoxy-5-aminophenyl; 2HCl] | Colorless crystal 182-185° C. (acetonitrile/ethanol/ether) [α]$_D$ −6.67° (c = 1.20, MeOH) | 2932, 2604, 1604, 1574, 1514, 1464, 1447, 1348, 1272, 1236, 1158, 1139, 1094, 1021, 978 | 1.91-2.13(4H, m), 2.80(1H, m), 3.11-3.26(4H, m), 3.65(2H, m), 3.79(2H, s), 3.90(3H, s), 3.93-4.02(2H, m), 4.44(1H, m), 6.93(1H, d), 7.04-7.11(5H, m), 7.17(3H, m), 7.24(2H, m) | MS(FAB/free base) m/z: 465(M + H$^+$) |
| 44 | [structure: 4-(4-fluorobenzyl)phenyl-piperazine linked via CH2-CH(OH)-CH2-O to 2-methoxy-5-aminophenyl; 3HCl] | Colorless crystal 196-198° C. (methanol/ether) [α]$_D$ −7.88° (c = 1.04, MeOH) | 2942, 2574, 1608, 1578, 1510, 1447, 1349, 1271, 1234, 1159, 1137, 1193, 1020 | 3.13-3.32(4H, m), 3.40(2H, m), 3.62-3.78(4H, m), 3.80(3H, s), 3.85(2H, s), 3.94-4.02(2H, m), 4.47(1H, m), 6.93(2H, d), 6.99(1H, dd), 7.06-7.12(6H, m), 7.22(2H, m) | $C_{27}H_{35}Cl_3FN_3O_3 \cdot 1/2H_2O$ (trihydrochloride)<br>　　C　　H　　N<br>Calcd: 55.54　6.04　7.20<br>Found: 55.55　6.01　7.21 |

TABLE 1-continued

| | Structure | Properties | IR | NMR | Analysis |
|---|---|---|---|---|---|
| 45 | [cyclopentyloxy-phenyl-piperidine-CH2-CH(OH)-CH2-O-phenyl(OMe)(NH2)] ·2HCl | Colorless crystal 184-187° C. (2-propanol/ether) [α]_D −9.14° (c = 1.16, MeOH) | 2950, 2598, 1612, 1579, 1514, 1447, 1354, 1268, 1244, 1168, 1136, 1023, 978 | 1.54-1.60(2H, m), 1.69-1.70(4H, m), 1.86-2.12(6H, m), 2.76(1H, m), 3.11-3.39(4H, m), 3.65(2H, m), 3.79(3H, s), 3.93-4.02(2H, m), 4.45(2H, m), 4.77(1H, m), 6.85(2H, d), 6.93(1H, dd), 7.05(2H, m), 7.13(2H, d) | MS(FAB/ free base) m/z: 441(M + H⁺) |
| 46 | [phenoxy-phenyl-piperidine-CH2-CH(OH)-CH2-O-dimethylphenyl-NH2] ·2HCl | Colorless crystal 227-228° C. (methanol/ether) [α]_D +1.2° (c = 0.68, MeOH) | 3287, 2743, 1589, 1508, 1489, 1452, 1316, 1244, 1173, 1148, 1092, 996, 866, 699 | 1.95-2.21(4H, m), 2.22(3H, s), 2.25(3H, s), 2.87(1H, m), 3.21(2H, m), 3.32(2H, m), 3.70(2H, m), 3.92(2H, m), 4.47(1H, m), 6.87(2H, m), 7.00(4H, d), 7.14(1H, t), 7.28(2H, d), 7.39(2H, t) | C₂₈H₃₆Cl₂N₂O₃ (dihydrochloride)<br>Calcd: C 64.74 H 6.98 N 5.39<br>Found: C 64.47 H 6.94 N 5.36 |
| 47 | [4-fluorobenzyl-phenyl-piperidine-CH2-CH(OH)-CH2-O-dimethylphenyl-NH2] ·2HCl | Colorless crystal 221-223° C. (2-propanol/ether) [α]_D −0.6° (c = 1.03, MeOH) | 1600, 1508, 1492, 1453, 1417, 1316, 1222, 1158, 1094, 1020, 970 | 1.95(2H, m), 2.03-2.16(2H, m), 2.22(3H, s), 2.24(3H, s), 2.81(1H, m), 3.13-3.21(2H, m), 3.26-3.46(2H, m), 3.67-3.70(2H, m), 3.91(4H, m), 4.45(1H, m), 6.84-6.89(2H, m), 7.10(2H, t), 7.18(4H, m), 7.23-7.27(2H, m) | C₂₈H₃₇Cl₂FN₂O₃·1/4H₂O (dihydrochloride)<br>Calcd: C 64.50 H 6.91 N 5.19<br>Found: C 64.59 H 6.87 N 5.25 |
| 48 | [4-fluorobenzyl-phenyl-piperazine-CH2-CH(OH)-CH2-O-dimethylphenyl-NH2] ·3HCl | Colorless crystal 220-221° C. (methanol/ether) [α]_D +2.77° (c = 1.01, MeOH) | 2852, 2584, 1602, 1508, 1499, 1460, 1415, 1316, 1223, 1157, 1093, 1016 | 2.24(3H, m), 2.27(3H, m), 3.34-3.69(10H, m), 3.84(2H, s), 3.92-4.00(2H, m), 4.49(1H, m), 6.94(2H, d), 7.01(2H, m), 7.05-7.13(4H, m), 7.20-7.24(2H, m) | C₂₈H₃₇Cl₃FN₂O₂ (trihydrochloride)<br>Calcd: C 58.70 H 6.51 N 7.33<br>Found: C 58.84 H 6.71 N 7.30 |

TABLE 1-continued

| | Structure | Properties | IR | NMR | MS/Analysis |
|---|---|---|---|---|---|
| 49 | [Structure: 4-phenoxyphenyl-piperidine with (S)-hydroxypropyl linker to 4-amino-5-chloro-2-methoxyphenoxy; 2HCl] | Colorless crystal 87-88° C. (ether/methylene chloride) [α]_D −25.1° (c = 0.35, MeOH) | 3344, 2933, 1676, 1590, 1508, 1490, 1443, 1240, 1201, 1180, 1136, 870, 834, 693 | 1.85-2.20(4H, m), 2.84(1H, m), 3.10-3.38(4H, m), 3.68(2H, m), 3.72(3H, s), 3.94(2H, m), 4.42(1H, m), 6.76(1H, s), 6.94(1H, s), 6.99(4H, d), 7.14(1H, t), 7.26(2H, d), 7.39(2H, t) | MS(FAB/free base) m/z:483(M + H⁺) |
| 50 | [Structure: 4-(4-fluorobenzyl)phenyl-piperazine with (S)-hydroxypropyl linker to 4-amino-5-chloro-2-methoxyphenoxy; 3HCl] | Colorless crystal 170-173° C. (ethanol/ether) [α]_D −6.42° (c = 1.09, MeOH) | 2844, 2584, 1611, 1514, 1442, 1403, 1357, 1271, 1221, 1180, 1158, 1136, 1092 | 3.11-3.41(6H, m), 3.61-3.80(4H, m), 3.75(3H, s), 3.84(2H, s), 3.89-3.97(2H, m), 4.43(1H, m), 6.93(2H, d), 7.01-7.12(6H, m), 7.20-7.24(2H, m) | C₂₇H₃₄Cl₄FN₃O₃ (trihydrochloride)<br>C H N<br>Calcd: 53.22 5.62 6.90<br>Found:53.49 5.54 6.97 |
| 51 | [Structure: 4-phenoxyphenyl-piperidine with (S)-hydroxypropyl linker to 4-amino-2,6-dichlorophenoxy; 2HCl] | Colorless crystal 196-198° C. (2-propanol/ether) [α]_D −12.4° (c = 0.5, MeOH) | 3328, 2936, 2595, 1589, 1508, 1489, 1479, 1420, 1240, 1170, 1014, 977, 870, 812, 751, 693 | 1.85-2.20(4H, m), 2.85(1H, m), 3.25(2H, m), 3.47(2H, m), 3.74(2H, m), 3.89(2H, m), 4.41(1H, m), 6.68(2H, m), 6.99(4H, m), 7.14(1H, t), 7.27(2H, d), 7.39(2H, t) | C₂₈H₃₀Cl₄N₂O₃ (dihydrochloride)<br>C H N<br>Calcd: 54.85 5.31 4.92<br>Found:54.96 5.26 4.94 |
| 52 | [Structure: 4-(4-fluorobenzyl)phenyl-piperazine with (S)-hydroxypropyl linker to 4-amino-2,6-dichlorophenoxy; 3HCl] | Colorless crystal 120-123° C. (ethanol/ether) [α]_D −22.8° (c = 1.06, MeOH) | 2840, 2584, 1614, 1603, 1508, 1477, 1456, 1400, 1281, 1251, 1217, 1158, 1138, 1292, 918, 813 | 3.10-3.35(6H, m), 3.45-3.50(2H, m), 3.61-3.81(4H, m), 3.84(2H, s), 3.86-3.90(2H, m), 6.675(2H, s), 6.93(2H, m), 7.10(4H, m), 7.22(2H, m) | MS(FAB/free base) m/z: 504(M + H⁺) |

TABLE 1-continued

| | Structure | Properties | IR | NMR | Elemental Analysis |
|---|---|---|---|---|---|
| 53 | (4-phenoxyphenyl piperidine with 2-methyl-4-methoxyanilino propanol) | Colorless crystal (dihydrochloride) 197-199° C. (methanol/ether) | (di-hydrochloride) 2952, 1590, 1510, 1491, 1294, 1267, 1244, 1202, 1170, 1136, 1108, 1073, 1049, 955 | 1.70-1.88(4H, m), 2.10(1H, m), 2.18(3H, s), 2.39-2.59(4H, m), 2.96(1H, m), 3.05(1H, m), 3.14(1H, m), 3.25(1H, m), 3.74(3H, s), 4.00-4.05(1H, m), 6.57(1H, m), 6.68-6.70(2H, m), 6.97(4H, m), 7.08(1H, t), 7.18(2H, d), 7.32(2H, m) | $C_{28}H_{30}Cl_2N_2O_3 \cdot 3/4H_2O$ (dihydrochloride)<br>C H N<br>Calcd: 64.55 6.96 5.38<br>Found: 64.54 6.93 5.34 |
| 54 | (4-fluorobenzyl phenyl piperidine with 2-methyl-4-methoxyanilino propanol) | Colorless crystal (dihydrochloride) 181-183° C. (ethanol/ether) | (di-hydrochloride) 2958, 1602, 1513, 1504, 1456, 1444, 1295, 1268, 1222, 1204, 1158, 1137, 1095, 1049, 1017 | 1.59-1.76(4H, m), 2.02(1H, m), 2.10(3H, s), 2.31-2.51(4H, m), 2.88(1H, m), 2.95-3.00(1H, m), 3.06(1H, m), 3.18(1H, dd), 3.67(3H, s), 3.85(2H, s), 3.92-3.96(1H, m), 6.49(1H, d), 6.61-6.63(2H, m), 6.89(2H, dt), 7.01-7.08(6H, m) | $C_{39}H_{37}Cl_2FN_2O_2 \cdot 1/4H_2O$ (dihydrochloride)<br>C H N<br>Calcd: 64.50 6.91 5.19<br>Found: 64.65 6.91 5.24 |
| 55 | (4-fluorobenzyl phenyl piperazine with 2-methyl-4-methoxyanilino propanol) | Colorless crystal (trihydrochloride) 183-185° C. (ethanol/ether) | (tri-hydrochloride) 2957, 2940, 1613, 1510, 1456, 1444, 1295, 1268, 1221, 1158, 1136, 1093, 1048, 966 | 2.17(1H, s), 2.47(1H, m), 2.57-2.63(3H, m), 2.80-2.85(2H, m), 3.04-3.08(1H, m), 3.16-3.20 (4H, m), 3.26(1H, m), 3.74(3H, s), 3.87(2H, s), 4.00-4.06(1H, m), 6.57(1H, d), 6.68-6.70(2H, m), 6.85(2H, d), 6.94(2H, t), 7.05(2H, d), 7.10-7.13(2H, m) | $C_{29}H_{37}Cl_3FN_3O_2$ (trihydrochloride)<br>C H N<br>Calcd: 58.70 6.51 7.33<br>Found: 58.52 6.62 7.29 |
| 56 | ((S)- 4-phenoxyphenyl piperidine with 2-methyl-4-methoxyanilino propanol) | Colorless crystal (dihydrochloride) 191-194° C. (methanol/ether) $[\alpha]_D -19.5°$ (c = 1.14, MeOH) | (di-hydrochloride) 2953, 1590, 1511, 1504, 1489, 1294, 1267, 1245, 1203, 1170, 1137, 1110, 1072, 1049, 951 | 1.69-1.88(4H, m), 2.10(1H, m), 2.18(3H, s), 2.40-2.60(4H, m), 2.96(1H, m), 2.55(1H, m), 3.14(1H, m), 3.26(1H, m), 3.75(3H, s), 4.01-4.05(1H, m), 6.57(1H, d), 6.68-6.71(2H, m), 6.98(4H, m), 7.08(1H, t), 7.18(2H, m), 7.33(2H, m) | $C_{28}H_{36}Cl_2N_2O_3 \cdot 1/4H_2O$ (dihydrochloride)<br>C H N<br>Calcd: 64.18 6.92 5.35<br>Found: 64.28 7.01 5.32 |
| 57 | ((R)- 4-phenoxyphenyl piperidine with 2-methyl-4-methoxyanilino propanol) | Colorless crystal (dihydrochloride) 188-191° C. (methanol/ether) $[\alpha]_D -19.5°$ (c = 1.12, MeOH) | (di-hydrochloride) 2953, 1590, 1510, 1493, 1456, 1294, 1268, 1246, 1203, 1170, 1137, 1101, 1072, 1048, 952 | 1.66-1.88(4H, m), 2.10(1H, m), 2.18(3H, s), 2.39-2.59(4H, m), 2.96(1H, m), 3.05(1H, m), 3.14(1H, m), 3.25(1H, m), 3.74(3H, s), 3.99-4.05(1H, m), 6.57(1H, d), 6.68-6.71(2H, m), 6.97(4H, m), 7.08(1H, t), 7.18(2H, m), 7.32(2H, m) | $C_{36}H_{36}Cl_2N_2O_3 \cdot 1/4H_2O$ (dihydrochloride)<br>C H N<br>Calcd: 64.18 6.92 5.35<br>Found: 64.24 6.91 5.38 |

TABLE 1-continued

| | Structure | Properties | IR | NMR | Analysis |
|---|---|---|---|---|---|
| 58 | [structure with phenoxy-phenyl-piperidine, CH2-CH(OH)-CH2-NH-tetramethyl-aminophenyl] 3HCl | Colorless crystal 221-223° C. (methanol/ether) | 3372, 2948, 1588, 1532, 1508, 1490, 1240, 1172, 1071, 951, 868, 748 | 1.95-2.20(4H, m), 2.17(6H, s), 2.22(1H, m), 2.28(6H, s), 2.86(1H, m), 2.96(1H, m), 3.10-3.50(6H, m), 4.48(1H, m), 6.99(4H, d), 7.14 (1H, t), 7.27(2H, d), 7.39(2H, t) | C₃₀H₄₂Cl₃N₃O₃·1/4H₂O (trihydrochloride)<br><br>　　C　　H　　N<br>Calcd: 61.33　7.21　7.15<br>Found: 61.33　7.09　7.16 |
| 59 | [structure with phenoxy-phenyl-piperidine, CH2-CH(OH)-CH2-O-chloro-trimethyl-aminophenyl] 3HCl | Colorless crystal 228-230° C. (methanol/ether) [α]_D −10.7° (c = 1.08, MeOH) | 2940, 1590, 1508, 1490, 1456, 1415, 1322, 1240, 1171, 1105, 1073, 1042, 977 | 1.95-2.11(4H, m), 2.16(3H, s), 2.22(3H, s), 2.30(3H, s), 2.83(1H, m), 3.14-3.45(4H, m), 3.67-3.80(4H, m), 4.44-4.46(1H, m), 6.99(4H, m), 7.14 (1H, t), 7.27(2H, d), 7.39(2H, t) | — |
| 60 | [structure with fluorobenzyl-phenyl-piperazine, CH2-CH(OH)-CH2-O-dimethyl-aminophenyl] 2HCl | Colorless crystal 197-198° C. (methanol/ether) [α]_D +8.36° (c = 1.33, MeOH) | 3384, 2928, 2599, 1627, 1600, 1508, 1460, 1327, 1287, 1219, 1127, 1017, 982, 824, 769 | 2.14(3H, s), 2.27(3H, s) 2.37(3H, s), 3.15-3.80(10H, m), 3.97(2H, m), 4.46(1H, m), 6.83(1H, s), 6.94(2H, d), 7.10(4H, m), 7.23(2H, dd) | — |
| 61 | [structure with phenoxy-phenyl-piperidine, CH2-CH(OH)-CH2-O-methoxy-methyl-aminophenyl] 2HCl | Colorless crystal 90-92° C. (ether/methylene chloride) [α]_D +8.24° (c = 1.09, MeOH) | 3384, 2936, 2599, 1590, 1520, 1471, 1447, 1349, 1236, 1167, 1021, 975, 870, 749 | 1.90-2.20(4H, m), 2.84(1H, m), 3.15-3.45(4H, m), 3.68(2H, m), 3.79(3H, s), 3.98(2H, m), 4.44(1H, m), 6.87(1H, d), 6.95-7.05(6H, m), 7.14(1H, t), 7.27(2H, d), 7.39(2H, t) | C₂₉H₃₇Cl₃N₂O₃·1/4H₂O (dihydrochloride)<br><br>　　C　　H　　N<br>Calcd: 60.84　6.51　4.89<br>Found: 60.79　6.48　4.91 |

TABLE 1-continued

| # | Structure | Properties | IR | NMR | Analysis |
|---|---|---|---|---|---|
| 62 | (4-fluorobenzyl-phenyl-piperazine with HO-CH2-CH(OH)-CH2-O-aryl-NH2, 2MeSO3H) | Colorless crystal 213-214° C. (2-propanol:water=20:1) $[\alpha]_D$ −7.8° (C = 1.3, MeOH) | 3307, 2913, 2620, 1614, 1564, 1506, 1460, 1327, 1214, 1160, 1042, 973, 808, 780 | 2.14(3H, s), 2.20(3H, s), 2.30(3H, s), 2.32(6H, s), 3.03-3.15(4H, m), 3.62(4H, m), 3.73(2H, m), 3.77(2H, s), 3.90-3.98(2H, m), 4.35(1H, m), 5.96(1H, brs), 6.79(1H, s), 6.94(2H, d), 7.07-7.14(4H, m), 7.23(2H, m) | $C_{31}H_{44}N_3O_8F_1S_2$ (dimethanesulfonate)<br>C H N<br>Calcd: 55.59 6.62 6.27<br>Found: 55.13 6.56 6.22 |
| 63 | (phenoxy-piperidine with OMe-aryl-NH2 chain, p-TsOH) | Colorless crystal 156-157° C. (methanol/ether) $[\alpha]_D$ −8.1° (C = 1.1, MeOH) | 3391, 3322, 3041, 1608, 1590, 1508, 1490, 1232, 1188, 1124, 1034, 1011 | 1.88(4H, m), 2.28(3H, s)s 2.83(1H, m), 3.09-3.23(4H, m), 3.60-3.65(2H, m), 3.65(3H, s), 3.83-3.93(2H, m), 4.30(1H, m), 5.86(1H, brs), 6.15(1H, dd), 6.32(1H, d), 6.67(1H, d), 6.97-7.00(4H, m), 7.09-7.15(3H, m), 7.25(2H, m), 7.39(2H, t), 7.47(2H, d) | $C_{34}H_{40}N_2O_7S_1$·3/4$H_2O$ (p-toluenesulfonate)<br>C H N<br>Calcd: 64.39 6.36 4.42<br>Found: 64.47 6.35 4.35 |
| 64 | (4-fluorobenzyl-phenyl-piperazine with aryl-NH2, 2HCl) | Colorless crystal 148-150° C. (2-propanol:water = 15:1) $[\alpha]_D$ −8.6° (C = 1.0, MeOH) | 3407, 2727, 2843, 1613, 1508, 1489, 1460, 1398, 1328, 1252, 1128, 909 | 2.12(3H, s), 2.21(3H, s), 2.30(3H, s), 3.24(4H, m), 3.57-3.80(6H, m), 3.84(2H, s), 3.92(2H, m), 4.44(1H, m), 5.97(1H, brs), 6.76(1H, s), 6.93(2H, d), 7.06-7.13(4H, m), 7.20-7.25(2H, m) | $C_{29}H_{38}N_3O_2F_1Cl_2$·3/4$H_2O$ (dihydrochloride)<br>C H N<br>Calcd: 61.75 6.79 7.45<br>Found: 61.82 6.83 7.38 |
| 65 | (4-fluorobenzyl-phenyl-piperazine with aryl-NH2, 1/2H2SO4) | Colorless crystal 154-157° C. (2-propanol:water = 3:1) $[\alpha]_D$ −10.8° (C = 1.1, $H_2O$) | 1615, 1508, 1490, 1460, 1398, 1321, 1255, 1040, 931, 808 | 2.01(3H, s), 2.07(3H, s), 2.08(3H, s), 3.10-3.45(10H, m), 3.79(2H, m), 3.84(2H, s), 4.26(1H, brs), 5.80(1H, brs), 6.54(1H, s), 6.92(2H, d), 7.06-7.12(4H, m), 7.21-7.25(2H, m) | MS(FAB/free base) m/z: 478(M + H⁺) |

TABLE 1-continued
| 66 | 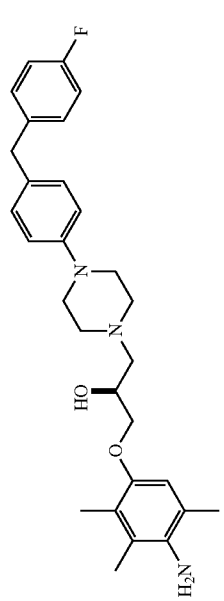 | Colorless crystal 163-168° C. (2-propanol:water = 15:1) $[\alpha]_D$ −6.2° (C = 1.2, MeOH) | 1630, 1508, 1460, 1415, 1328, 1191, 1124, 1082, 1064, 884, 834, | 2.14(3H, s), 2.21(3H, s), 2.32(3H, s), 3.02-3.42(6H, m), 3.61-3.63(2H, m), 3.72-7.80(2H, m), 3.84(2H, s), 3.95(2H, m), 4.35(1H, m), 6.80(1H, s), 6.93(2H, m), 7.07-7.13(4H, m), 7.21-7.25(2H, m) | MS (FAB/free base) m/z: 478(M + H⁺) |
|---|---|---|---|---|---|
| |  H₂SO₄ | | | | |

Inhibitory Effect of Veratrizine-Induced Sodium Channel Activity

The membrane potential of the synaptozomes prepared from the brain membrane of Wistar rats (male, 10 to 12 weeks old) was measured by the method of Aiuchi et al. [T. Aiuchi et al: Biochimi. Biophys. Acta. 771, 228 (1984)] using a membrane sensitive fluorescent dye Rhodamine 6G to evaluate the effects of suppression of the compound on the veratrizine-inducing depolarization response. The results are shown in Table II.

TABLE II

| Compound no. | Anti-veratrizine effect (inhibiting rate %) (compound 0.1 μM) |
|---|---|
| 25 | 21 |
| 26 | 42.2 |
| 27 | 32.1 |
| 28 | 27.9 |
| 30 | 23.5 |
| 31 | 20 |
| 32 | 14.5 |
| 33 | 19.5 |
| 34 | 17.2 |
| 35 | 23.2 |
| 36 | 23.3 |
| 37 | 24.3 |
| 38 | 43.9 |
| 40 | 33.9 |
| 41 | 22.1 |
| 42 | 10.3 |
| 43 | 21 |
| 44 | 12.2 |
| 46 | 29.4 |
| 47 | 30.5 |
| 48 | 17.5 |
| 49 | 15.1 |
| 51 | 39.8 |
| 53 | 23.8 |
| 54 | 24.2 |
| 55 | 21.3 |
| 56 | 28.5 |
| 57 | 25.8 |
| 58 | 25.8 |

T-Type Calcium Channel Inhibitory Effect

The hippocampal CA1 pyramidal cells were isolated from Wistar rats (female, 1 week old) in according to the method reported by Takahashi et al. [K. Takahashi et al.; J. Pharmacol. Exp. Ther., 256, 169 (1991)] and the T-type calcium current was measured under conditions of a fixed membrane potential using the whole-cell configuration of the patch clamp technique. The effects of the compounds were evaluated from the rate of suppression of the peak current after 1 minute of application using the concentration clamp method. The results are shown in Table III.

TABLE III

| Compound no. | T-type $Ca^{2+}$ channel inhibitory effect $IC_{50}$ (μM) |
|---|---|
| 26 | 3.4 |
| 28 | 3.0 |
| 41 | 4.0 |
| 53 | 2.2 |

Lipid Peroxidation Suppression Effect

The whole brains of Wistar rats (10 weeks old, male) were excised and homogenized in the 10 times volumes of 50 mM phosphate-buffered solution (pH=7.4.) (hereinafter referred to as PBS). The centrifuged supernatant was further diluted fourfold and the result was used as the brain membrane preparation. The membrane preparation was incubated in the presence of vehicle (0.5% DMSO) or compound at 37° C. for 30 minutes and an automatic oxidation reaction promoted. The reaction was stopped by 35% perchloric acid, then the total of the main decomposition products of the peroxidized lipids present in the centrifuged supernatent, that is, malonaldehyde and 4-hydroxyalkenals, was measured using a BIOXY-TECH$^{(R)}$/LPO-586™ peroxidized lipid colorimetric assay kit (OXIS International, Inc.) and used as an indicator of the lipid peroxidation. The $IC_{50}$ value was found from the curve of the concentration for suppressing production of these aldehydes in the presence of the compound.

The results are shown in Table IV.

TABLE IV

| Compound no. | Lipid peroxidation suppressing effect $IC_{50}$ (μM) |
|---|---|
| 26 | 0.25 |
| 27 | 0.46 |
| 28 | 0.22 |
| 29 | 0.38 |
| 34 | 0.80 |
| 37 | 0.86 |
| 38 | 3.6 |
| 39 | 0.72 |
| 40 | 3.6 |
| 41 | 0.87 |
| 46 | 8.6 |
| 53 | 0.27 |
| 58 | 0.37 |
| Flunarizine | 42 |

Dopamine $D_2$ Receptor Blocking Action

57 μl of the membrane fraction prepared from the striatum of Wistar male rats (6 weeks old) was incubated together with the compound and 1.0 nM [$^3$H] raclopride in a buffer at 25° C. for 1 hour. A GF/C glass filter (0.1% polyethylene imine treatment) was used for B/F separation. A beta plate was used for measurement of the radioactivity to evaluate the effect of the compound.

The results are shown in Table V.

TABLE V

| Compound no. | Dopamine $D_2$ receptor blocking action $IC_{50}$ (nM) |
|---|---|
| 26 | 5600 |
| 27 | 6300 |
| 28 | 12000 |
| 40 | 12000 |
| 41 | 11000 |
| 53 | 11000 |
| Flunarizine | 228 |

Audiogenic Seizure Suppressing Effect

The audiogenic seizure suppressing effect of the compounds was evaluated by the method of Sarro et al. [G. B. De Sarro et al., Br. J. Pharmacol., 93, 247 (1988)]. That is, the compound dissolved in 10% 2-hydroxypropyl-β-cyclodextrin was administered intraperitoneally to DBA/2N type mice (male, 3 weeks old). After 20 minutes, a supersonic washer was used to apply audio stimulus of at least 90 dB for 1 minute. The wild running (WR), clonic seizures (clonus), tonic seizures (tonus), and the respiratory arrest (RA) were observed. The seizure suppressing effect was evaluated from the rate of suppression of the average value of the seizure score found as 0=no response, 1=WR, 2=clonus, 3=tonus, and 4=RA. The results are shown in Table VI.

TABLE VI

| Compound no. | Antiseizure effect (suppression rate %) (compound 10 mg/kg, i.p.) |
| --- | --- |
| 25 | 58 |
| 26 | 74 |
| 27 | 55 |
| 28 | 76 |
| 30 | 44 |
| 31 | 74 |
| 32 | 70 |
| 33 | 78 |
| 34 | 74 |
| 35 | 74 |
| 36 | 68 |
| 37 | 76 |
| 38 | 92 |
| 40 | 80 |
| 41 | 60 |
| 42 | 50 |
| 43 | 30 |
| 44 | 80 |
| 45 | 44 |
| 46 | 88 |
| 47 | 56 |
| 48 | 70 |
| 49 | 42 |
| 51 | 74 |
| 53 | 46 |
| 54 | 58 |
| 55 | 70 |
| 56 | 64 |
| 57 | 68 |
| 58 | 68 |

Acute Toxicity Test

A pharmaceutical preparation was administered intravenously to ddY mice (male, 6 weeks old). The 50% lethal dosage $LD_{50}$ of the acute toxicity was calculated by an ordinary method from the death rate up to 24 hours after administration. The results are shown in Table VII.

TABLE VII

| Compound no. | $LD_{50}$ (mg/kg, i.v.) |
| --- | --- |
| 26 | 41 |
| 28 | 47.3 |
| 40 | 49.1 |
| 41 | 36.7 |

INDUSTRIAL APPLICABILITY

As explained above, the arylpiperidinopropanol and arylpiperazinopropanol derivatives represented by the formula (I) according to the present invention have effects suppressing cytotoxic $Ca^{2+}$ overload and lipid peroxidation, are high in safety, and are useful as pharmaceuticals for the alleviation or treatment of ischemic diseases.

The invention claimed is:

1. A method for the alleviation or treatment of symptoms due to neurodegenerative diseases which are selected from the group consisting of Parkinson's disease and amyotrophic lateral sclerosis comprising administering to a patient in need of such alleviation or treatment an effective amount of a pharmaceutical composition containing, as an effective ingredient, a compound having the formula (I) or its pharmaceutically acceptable salt, hydrate, or hydrate salt:

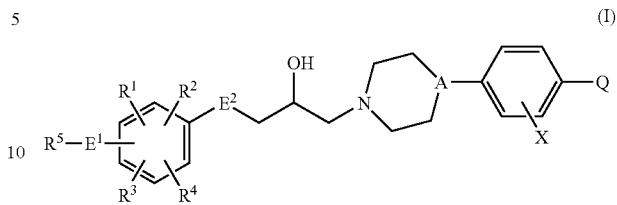

(I)

wherein
$R^1$ to $R^4$ independently represent a hydrogen atom, a halogen atom, a hydroxy group, an alkoxy group, an alkyl group, or an alkyl group substituted with a halogen atom,
$R^5$ represents a hydrogen atom, an alkyl group, or an alkyl group substituted with a halogen atom,
$E^1$ represents —NH,
$E^2$ represents an oxygen atom,
A represents a nitrogen atom,
X represents a hydrogen atom, a halogen atom, an alkoxy group, an alkyl group, or an alkyl group substituted with a halogen atom, and
Q represents a phenyl group, a phenyl group substituted with a substituent selected from the group consisting of a halogen atom, a hydroxyl group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenoxy group, a phenoxy group substituted with a substituent selected from the group consisting of a halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenylmethyl group, or a phenylmethyl group substituted with a substituent selected from the group consisting of a halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom,
and a carrier therefor.

2. A method as claimed in claim 1, wherein said pharmaceutical composition is orally or non-orally administered.

3. A method as claimed in claim 1, wherein, in the formula (I), $R^1$ to $R^4$ each independently represent a hydrogen atom, a halogen atom, an alkoxy group, or an alkyl group or an alkyl group substituted with a halogen atom, $R^5$ represents a hydrogen atom or an alkyl group or an alkyl group substituted with a halogen atom, $E^1$ represents NH, and $E^2$ represents an oxygen atom.

4. A method as claimed in claim 1, wherein, in the formula (I), $R^1$ to $R^4$ each independently represent a hydrogen atom, a halogen atom, an alkoxy group, or an alkyl group or an alkyl group substituted with a halogen atom, $R^5$ represents a hydrogen atom or an alkyl group or an alkyl group substituted with a halogen atom, $E^1$ represents an oxygen atom, and $E^2$ represents NH.

5. A method as claimed in claim 1, wherein, in the formula (I), one of $R^1$ to $R^4$ is a hydrogen atom and the others each independently represent a halogen atom, an alkoxy group, or an alkyl group or an alkyl group substituted with a halogen atom.

6. A method as claimed in claim 1, wherein, in the formula (I), Q represents a phenyl group, a phenyl group substituted with a substituent selected from the group consisting of a 'halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenoxy group, a phenoxy group substituted with a substituent selected from the group consisting of a halogen atom, a hydroxyl group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenylmethyl group, or a phenylmethyl group substituted with a substituent selected from the group consisting of a halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom.

7. A method for suppressing cell death in a patient having a neurodegenerative disease selected from the group consisting of Parkinson's disease and amyotrophic lateral sclerosis comprising:

administering to said patient in need thereof an effective amount of a pharmaceutical composition containing, as an effective ingredient, a compound having the formula (I) or its pharmaceutically acceptable salt, hydrate, or hydrate salt:

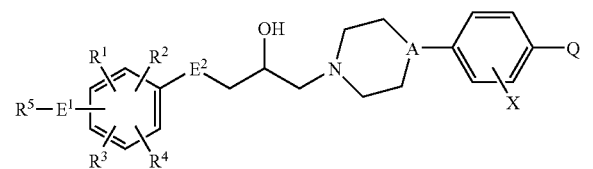

(I)

wherein $R^1$ to $R^4$ independently represent a hydrogen atom, a halogen atom, a hydroxy group, an alkoxy group, an alkyl group, or an alkyl group substituted with a halogen atom, $R^5$ represents a hydrogen atom, an alkyl group, or an alkyl group substituted with a halogen atom, $E^1$ represents —NH, $E^2$ represents an oxygen atom, A represents a nitrogen atom, X represents a hydrogen atom, a halogen atom, an alkoxy group, an alkyl group, or an alkyl group substituted with a halogen atom, and Q represents a phenyl group, a phenyl group substituted with a substituent selected from the group consisting of a halogen atom, a hydroxyl group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenoxy group, a phenoxy group substituted with a substituent selected from the group consisting of a halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom, a phenylmethyl group, or a phenylmethyl group substituted with a substituent selected from the group consisting of a halogen atom, a hydroxy group, a $C_1$ to $C_5$ linear or branched alkoxy group, a $C_1$ to $C_5$ linear or branched alkyl group, a $C_1$ to $C_5$ linear or branched alkyl group substituted with a halogen atom, and a carrier therefor.

* * * * *